(12) United States Patent
Potts et al.

(10) Patent No.: US 8,044,255 B2
(45) Date of Patent: Oct. 25, 2011

(54) TREATMENT OF PERSONAL CARE PRODUCTS TO REDUCE LEAKAGE

(75) Inventors: David Charles Potts, Dunwoody, GA (US); Jack Nelson Lindon, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 761 days.

(21) Appl. No.: 11/611,622

(22) Filed: Dec. 15, 2006

(65) Prior Publication Data

US 2008/0147024 A1    Jun. 19, 2008

(51) Int. Cl.
*A61F 13/15* (2006.01)

(52) U.S. Cl. .............. 604/359; 604/360; 604/385.101; 604/378; 604/381; 604/382; 604/367

(58) Field of Classification Search .............. 604/359, 604/360, 385.101, 378, 381, 382, 367; 424/76.1, 424/76.2, 76.3, 76.4
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 4,041,203 A | 8/1977 | Brock et al. |
| 4,340,563 A | 7/1982 | Appel et al. |
| 4,374,888 A | 2/1983 | Bornslaeger |
| 4,375,448 A | 3/1983 | Appel et al. |
| 4,488,928 A | 12/1984 | Ali Khan et al. |
| 4,494,278 A | 1/1985 | Kroyer et al. |
| 4,640,810 A | 2/1987 | Laursen et al. |
| 5,108,820 A | 4/1992 | Kaneko et al. |
| 5,108,827 A | 4/1992 | Gessner |
| 5,169,706 A | 12/1992 | Collier, IV et al. |
| 5,336,552 A | 8/1994 | Strack et al. |
| 5,382,400 A | 1/1995 | Pike et al. |
| 5,527,171 A | 6/1996 | Soerensen |
| 5,883,231 A | 3/1999 | Achter et al. |
| 5,895,710 A * | 4/1999 | Sasse et al. ................ 442/334 |
| 6,060,636 A | 5/2000 | Yahiaoui et al. |

(Continued)

FOREIGN PATENT DOCUMENTS

WO    9809662 A    3/1998

(Continued)

OTHER PUBLICATIONS

International Search Report and Written Opinion for PCT/IB2007/054640 mailed Mar. 30, 2009.

*Primary Examiner* — Jacqueline F. Stephens

(74) *Attorney, Agent, or Firm* — Armstrong Teasdale LLP

(57) ABSTRACT

The present disclosure relates to personal care products such as diapers, training pants, feminine care articles, incontinence articles, bandages, and the like, that have been treated to enhance liquid intake and distribution performance characteristics and reduce leakage. Advantageously, the treated personal care products described herein not only reduce the viscosity and elasticity of viscoelastic fluids that come in contact with the treated product, but also reduce the fouling effect of such fluids.

10 Claims, 11 Drawing Sheets

U.S. PATENT DOCUMENTS

| | | | |
|---|---|---|---|
| 6,656,928 B1 * | 12/2003 | McCadden | 514/167 |
| 2001/0055681 A1 * | 12/2001 | Phillips et al. | 428/364 |
| 2002/0120241 A1 * | 8/2002 | Tyrrell et al. | 604/364 |
| 2004/0186448 A1 | 9/2004 | Misek et al. | |
| 2005/0113772 A1 | 5/2005 | La Fortune | |

FOREIGN PATENT DOCUMENTS

| | | |
|---|---|---|
| WO | 0126596 A | 4/2001 |
| WO | 0249686 A | 6/2002 |
| WO | 2005035013 A | 4/2005 |

\* cited by examiner

TREATMENT OF PERSONAL CARE PRODUCTS TO REDUCE LEAKAGE

BACKGROUND OF DISCLOSURE

The present disclosure generally relates to personal care products such as diapers, training pants, feminine care articles, incontinence articles, bandages, and the like, and more particularly to such products that have been treated to enhance liquid intake and distribution performance characteristics and reduce leakage.

A wide variety of disposable absorbent articles for collecting bodily fluids are known in the art. Examples of such articles include disposable diapers and training pants, feminine hygiene products, such as sanitary napkins and tampons, incontinent care products such as pads and undergarments, and wound dressing products, such as bandages.

One problem associated with absorbent articles is their tendency to leak before the liquid absorbent capacity of the entire absorbent article is fully used. Leakage typically results from the inability of the absorbent article to fully intake liquids rapidly and completely when large amounts of liquids are discharged into the article. Another problem that may contribute to leakage is the inability of the absorbent core of the article to move or distribute sufficient amounts of liquid between discharges from a target area portion of the absorbent core to more distal and more remote end regions of the absorbent core which have not been used. This results in saturation of only the central target area of the absorbent core, which may in turn result in poor performance and leakage of the product. Consequently, there is a continuing effort by absorbent article manufacturers to improve the liquid intake and distribution performance of absorbent articles to thereby reduce the tendency of such articles to leak as they become increasingly saturated during use, particularly where the article is subjected to repeated liquid insults before being discarded.

Certain fluids, such as menses, have viscoelastic properties that make obtaining good intake and distribution performance particularly problematic. In particular, the relatively high viscosity and/or elasticity of such fluids tends to interfere with the absorption and distribution of the fluids within the absorbent article. In other instances, intake performance of an absorbent article may be impeded when components of the menses block the open channels between superabsorbent particles or fibers contained in the absorbent article. This phenomenon is often referred to as fouling. Attempts have been made to improve absorption and distribution of fluids with high viscoelastic properties by modifying the viscoelastic properties of the fluid itself. However, treatments that reduce viscoelasticity do not always improve fluid distribution and intake into absorbent articles, and may have no effect on fouling, and in certain instances, may even increase the fouling effect of the fluid.

Based on the foregoing, there is a need in the art for a treatment that may be used in connection with personal care products, such as absorbent articles, that provides products that have an improved intake and distribution performance, and reduced leakage. Additionally, it would be advantageous if the treatment not only reduced the viscoelastic properties of the fluid being absorbed, but also decreased the fouling effect of the fluid.

SUMMARY OF THE DISCLOSURE

The present disclosure relates to personal care products such as diapers, training pants, feminine care articles, incontinence articles, bandages, and the like, that have been treated to enhance liquid intake and distribution performance characteristics and reduce leakage. Advantageously, the treated personal care products described herein not only reduce the viscosity and elasticity of viscoelastic fluids that come in contact with the treated product, but also reduce the fouling effect of such fluids.

In one aspect, the present disclosure is directed to a personal care product for receiving a fluid having viscoelastic properties, the personal care product comprising a substrate and a treatment agent selected from the group consisting of polyethylene glycol 600 lauryl ether, polyethylene glycol 600 monolaurate, and combinations thereof.

In another aspect, the present disclosure is directed to a personal care product for receiving a fluid having viscoelastic properties, the personal care product comprising a substrate and a polyethylene glycol derivative, wherein the polyethylene glycol derivative is capable of reducing the viscosity and elasticity of the fluid.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
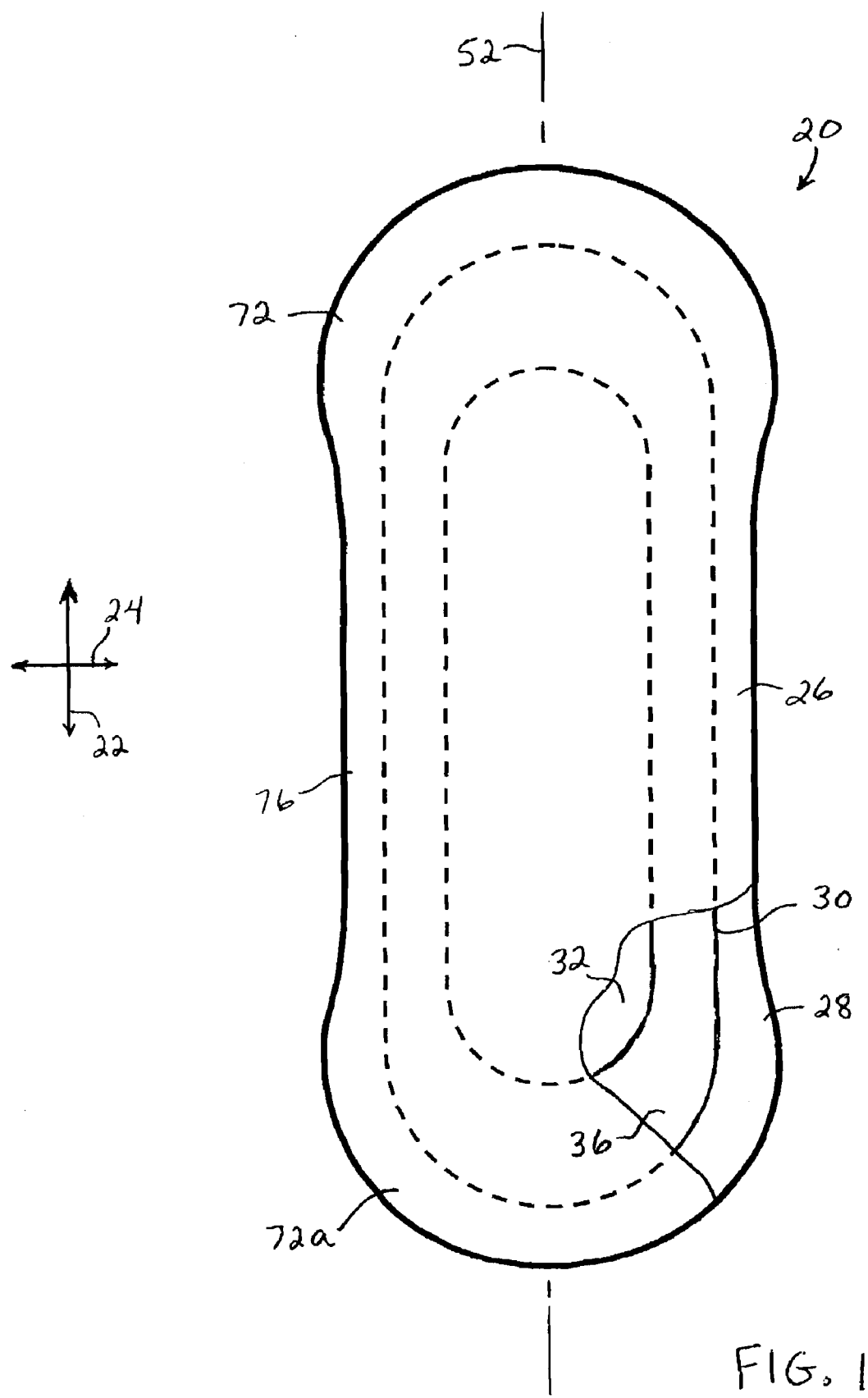
FIG. 1 shows a representative, partially cut-away, top, plan view of a garment-side of an absorbent article in which separately side-panels or wings are assembled to the article and arranged in a storage position.

The present disclosure is generally directed to structures that are particularly adapted to receive fluids having viscoelastic properties, such as menses, mucous, blood products, and feces, among others, and personal care products comprising these structures, that have been treated to improve fluid intake, distribution, and absorption properties and decrease leakage. Advantageously, the treated structures described herein are capable of reducing not only the viscosity and elasticity of viscoelastic fluids that come in contact therewith, but also the fouling effect of such fluids.

As noted above, the relatively high viscosity and elasticity of viscoelastic fluids tends to interfere with the absorption and distribution of these fluids within absorbent articles, oftentimes resulting in leaking of the absorbent article. Attempts have been made to improve fluid intake and distribution properties of absorbent products by applying thereto viscoelastant agents that are capable of reducing the viscosity and/or elasticity of viscoelastic fluids. See U.S. Pat. No. 6,060,636. However, viscoelastant agents that are effective at reducing viscosity and elasticity of viscoelastic fluids are not always effective at reducing the fouling effects of these fluids and may, in certain instances, actually increase the fouling effect.

As used herein, "fouling" means the change in permeability of a fluid as it passes through a porous medium. More particularly, fouling is the reduction in permeability that occurs when components of a fluid pass through a porous medium and interact with the material structure, decreasing the inherent permeability of the porous material. Fouling may be measured as described in the Examples.

Without wishing to be bound to any particular theory, it is believed that fouling by viscoelastic fluids such as menses is likely due to mucin globules present in the fluid. Mucin is a large glycoprotein present in mucus-like fluids that gives the fluids most of their mucous-like properties. Mucin can exist in both a soluble form in the fluid and as mucin globules. Mucin globules are typically in the range of about 50 to about 200 microns in size, and comprise gelled or aggregated mucin molecules. Viscoelastant agents may act in several ways to reduce fouling. For example, it is believed that some viscoelastant agents dissolve the mucin aggregates and significantly reduce the number of these globules, resulting in a reduction in fouling. Examples of such viscoelastant agents include polyethylene glycol laurates. Other viscoelastant agents may act to reduce the effects of the soluble mucin molecules that produce the elastic or "stringy" quality of menses, but have little or no effect on the mucin globules. Other viscoelastant agents may have both effects.

In contrast, some viscoelastant agents, as noted above, may actually increase fouling effects. Such agents may act by increasing the size of mucin globules by partially solubilizing the mucin in the globules, reducing but not eliminating the interactions that bind the molecules into globules. These partial effects may allow the globules to swell without breaking down completely, thus increasing the sizes of the mucin globules and increasing the fouling effect.

It has now been discovered that certain surfactants, such as polyethylene glycol 600 lauryl ether and related compounds and polyethylene glycol 600 monolaurate and related compounds are not only effective viscoelastant agents, i.e., are capable of reducing the viscosity and elasticity of viscoelastic fluids, but also reduce the fouling effects of viscoelastic fluids. These surfactants may be applied to the structures and personal care products described herein to improve fluid intake and distribution performance and reduce leakage.

In one embodiment, the treated structure comprises a nonwoven web or fabric. The fibers from which the fabric is made may be produced, for example, by the meltblowing or spunbonding processes, including those producing bicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving formations mat or belt to form the nonwoven fabric. The fibers produced in the spunbond and meltblown processes are microfibers as defined herein.

The nonwoven also may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

The nonwoven may also be produced through airlaying. The production of airlaid nonwovens is well defined in the literature and documented in the art. Examples include the DanWeb process as described in U.S. Pat. No. 4,640,810 to Laursen et al., the Kroyer process as described in U.S. Pat. No. 4,494,278 to Kroyer et al., U.S. Pat. No. 5,527,171 to Soerensen, and the method of U.S. Pat. No. 4,375,448 to Appel et al., or other similar methods.

The fabric used in this disclosure may be a multilayer laminate. An example of multilayer laminate is an embodiment wherein some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al, and U.S. Pat. No. 4,374,888 to Bornslaeger. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. The treatment in accordance with the disclosure may be carried out inline with the nonwoven manufacturing process or offline on previously produced substrates or nonwovens.

Spunbond nonwoven fabrics are generally bonded in some manner as they are produced in order to give them sufficient structural integrity to withstand the rigors of further processing into a finished product. Bonding can be accomplished in a number of ways such as hydroentanglement, needling, ultrasonic bonding, adhesive bonding, stitchbonding, through-air bonding and thermal bonding.

As noted above, the structures described herein are advantageously treated with an agent that is not only an effective viscoelastant, i.e., is capable of reducing the viscosity and elasticity of viscoelastic fluids, but also improves the fouling effects of viscoelastic fluids. Preferably, the treatment agent will reduce both viscosity and elasticity of viscoelastic fluids that come in contact with the treatment agent by at least about 10%, more preferably by at least about 30%, more preferably by at least about 40%, more preferably by at least about 50%, more preferably by at least about 60%, and still more preferably by at least about 70% as compared to untreated viscoelastic fluids, when measured at a temperature of 22° C., a shear rate of $1.0 \text{ sec}^{-1}$, and a frequency of 0.1 Hertz. Additionally, the treatment agent will also preferably reduce the fouling properties of viscoelastic fluids that come in contact with the treatment agent by at least about 20%, more preferably by at least about 40%, and more preferably by at least about 50% as compared to untreated viscoelastic fluids.

It should be recognized that the treatment agents described herein may exert various combinations of effects on viscosity, elasticity, and fouling, depending on the concentration at which they are applied to the substrate.

In one embodiment, the treatment agent is selected from the group consisting of polyethylene glycol laurates, polyethylene glycol lauryl ethers, and combinations thereof. Advantageously, the polyethylene glycol laurates and polyethylene glycol lauryl ethers are capable of reducing both the viscosity and elasticity of viscoelastic fluid. Examples of suitable polyethylene glycol laurates include polyethylene glycol 400 monolaurate, polyethylene glycol 600 monolaurate, polyethylene glycol 1000 monolaurate, polyethylene glycol 4000 monolaurate, polyethylene glycol 600 dilaurate, and combinations thereof. Examples of suitable polyethylene glycol lauryl ethers include polyethylene glycol 600 lauryl ether. Preferably, the polyethylene glycol lauryl ether and/or polyethylene glycol laurate treatment agent is further capable of reducing the fouling properties of viscoelastic fluid. Particularly preferred examples of treatment agents include polyethylene glycol (PEG) 600 lauryl ether and related compounds, polyethylene glycol (PEG) 600 monolaurate and related compounds, and combinations thereof.

In addition to the PEG laurates and PEG lauryl ethers, other polyethylene glycol derivatives may be viscoelastic agents (i.e., are capable of reducing the viscosity and elasticity of viscoelastic fluids) and may be used as treatment agents for the personal care products described herein. As used herein, the term "polyethylene glycol derivative" includes any compound comprising a polyethylene glycol moiety. Examples of other suitable PEG derivatives include PEG monostearates such as PEG 200 monostearates and PEG 4000 monostearate; PEG dioleates such as PEG 600 dioleate and PEG 1540 dioleate; PEG monooleates such as PEG 600 monooleate and PEG 1540 monooleate; PEG monoisostearates such as PEG 200 monoisostearate; and PEG 16 octyl phenyl. Particularly preferred polyethylene glycol derivatives for use as treatment agents are those that improve intake time of viscoelastic fluids as well as reduce viscosity and elasticity. Examples of preferred PEG derivatives include PEG 1540 dioleate, PEG 600 monooleate, PEG 1540 monooleate, and PEG 16 octyl phenyl. These PEG derivatives may be used alone or in combination with PEG 600 monolaurate, PEG 600 lauryl ether, and/or other viscoelastic agents as a treatment agent.

In certain embodiments, the treatment agents described herein, such as polyethylene glycol 600 lauryl ether and/or the polyethylene glycol 600 monolaurate, may be used in combination with each other or in combination with other viscoelastant agents. Examples of additional viscoelastant agents that may be used in combination with the treatment agents include sodium citrate, dextran, cysteine, Glucopon 220UP (available as a 60% (by weight) solution of alkyl polyglycoside in water from Henkel Corporation), Glucopon 425, Glucopon 600, Glucopon 625. Other suitable viscoelastant agents are described in U.S. Pat. No. 6,060,636, herein incorporated by reference in its entirety. Surprisingly, it has been discovered that certain viscoelastant agents that actually increase the fouling effect of viscoelastic fluids when used alone, will in fact improve fouling effects when used in combination with PEG 600 lauryl ether and/or PEG 600 monolaurate. For example, in one embodiment, sodium citrate may be used in combination with PEG 600 monolaurate as a treatment agent. When two or more treatment agents are used in combination, the proportion of each treatment agent applied to the personal care product is preferably in a ratio of from about 1:2 to about 2:1, and more preferably is about 1:1.

The treatment agent may be applied in varying amounts depending on the desired results and application. Typically, the treatment agent is applied to the substrate in an amount of from about 0.1% (by weight of the treated substrate) to about 40% (by weight of the treated substrate), more preferably in an amount of from about 0.1% (by weight of the treated substrate) to about 20% (by weight of the treated substrate), and still more preferably in an amount of from about 3% (by weight of the treated substrate) to about 12% (by weight of the treated substrate).

Substrates treated with the treatment agent may be incorporated into personal care products as, for example, a cover (i.e., a body contact layer), a distribution or intake layer between a cover and an absorbent layer (e.g., an absorbent core or body), an absorbent layer, or any other suitable layer such as described herein, or in more than one of these layers. If the treatment agent is applied to a body contact layer, the add-on amount is preferably from about 0.1% (by weight of the treated substrate) to about 40% (by weight of the treated substrate), more preferably about 3% (by weight of the treated substrate) to about 20% (by weight of the treated substrate), and more preferably from about 10% (by weight of the treated substrate) to about 20% (by weight of the treated substrate). For intake/distribution layer applications, effective results are obtained within a range of about 0.1% (by weight of the treated substrate) to about 20% (by weight of the treated substrate), with a range of about 3% (by weight of the treated substrate) to about 12% (by weight of the treated substrate) being preferred. For absorbent layer applications, the add-on amount of treatment agent is preferably from about 0.1% (by weight of the treated substrate) to about 30% (by weight of the treated substrate), and preferably from about 3% (by weight of the treated substrate) to about 12% (by weight of the treated substrate).

As will be recognized by those skilled in this art, many substrate materials may be treated in accordance with the invention including nonwovens such as spunbond, meltblown, carded webs, airlaids, and others as well as woven webs and even films and the like where improved fluid distribution is desired. It will also be recognized by those skilled in this art that some treatment agents may be used as internal additives, that is, added to the polymer melt directly or in a concentrate form. After fiber formation, such additives will migrate to the fiber surface and impart the desired effect. For further discussion of internal addition of additives, reference may be had to U.S. Pat. No. 5,540,979 to Yahiaoui, et al., the contents of which are incorporated entirely herein by reference.

The treatment agent may be applied to the substrate by any suitable means including, for example, spraying, e.g., using an atomizer, by a "dip and nip" process, a kiss roller, printing, and various direct applications such as knife coating, blade coating (e.g., doctor blades), and the like. The treatment agents may also be used as internal additives, i.e., added to the polymer melt directly or in a concentrate form during formation of a non-woven fabric. Examples of suitable methods of applying the treatment agent are also described in the Examples.

Other additives may also be applied to the substrate along with the treatment agent for the desired result so long as the additives do not have a major detrimental effect on the activity of the treatment agent. Examples of such additives include additional conventional surfactants such as ethoxylated hydrocarbons or ionic surfactants, or co-wetting aids such as low molecular weight alcohols.

As noted above, the treated structures described herein may be incorporated into personal care products as, for example, a body contact liner, a distribution layer between a liner and an absorbent layer, an absorbent layer, etc., or in more than one of these layers. Examples of personal care products include feminine hygiene products like sanitary wipes and menses absorbing devices (e.g., sanitary napkins and tampons), infant and child care products such as disposable diapers, absorbent underpants, and training pants, wound dressings such as bandages, incontinent products, products for wiping and absorbing oils, and the like.

In one particular embodiment, the treated substrate is incorporated into a feminine hygiene product. Although the present disclosure is discussed primarily in combination with feminine hygiene products such as feminine napkins, panty liners, tampons, and interlabial pads, it will be readily apparent to one skilled in the art based on the disclosure that the products and methods described herein can also be used in combination with numerous other absorbent articles. As used herein, the phrase "absorbent article" generally refers to devices which absorb and contain body fluids, and more specifically, refers to devices which are placed against or near the skin to absorb and contain the various fluids discharged from the body and, in particular, viscoelastic fluids. Examples of absorbent articles include absorbent articles intended for personal wear, such as diapers; incontinence products; feminine hygiene products, such as feminine napkins, panty liners, tampons, and interlabial pads; other personal garments; and the like.

Disposable absorbent articles such as, for example, many of the feminine care absorbent products, can include a liquid pervious topsheet (also referred to herein as a cover or body contact layer), a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, the body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn. Suitable absorbent articles are described in U.S. Patent Application No. 2004/0186448, herein incorporated by reference in its entirety.

Figure 1A:
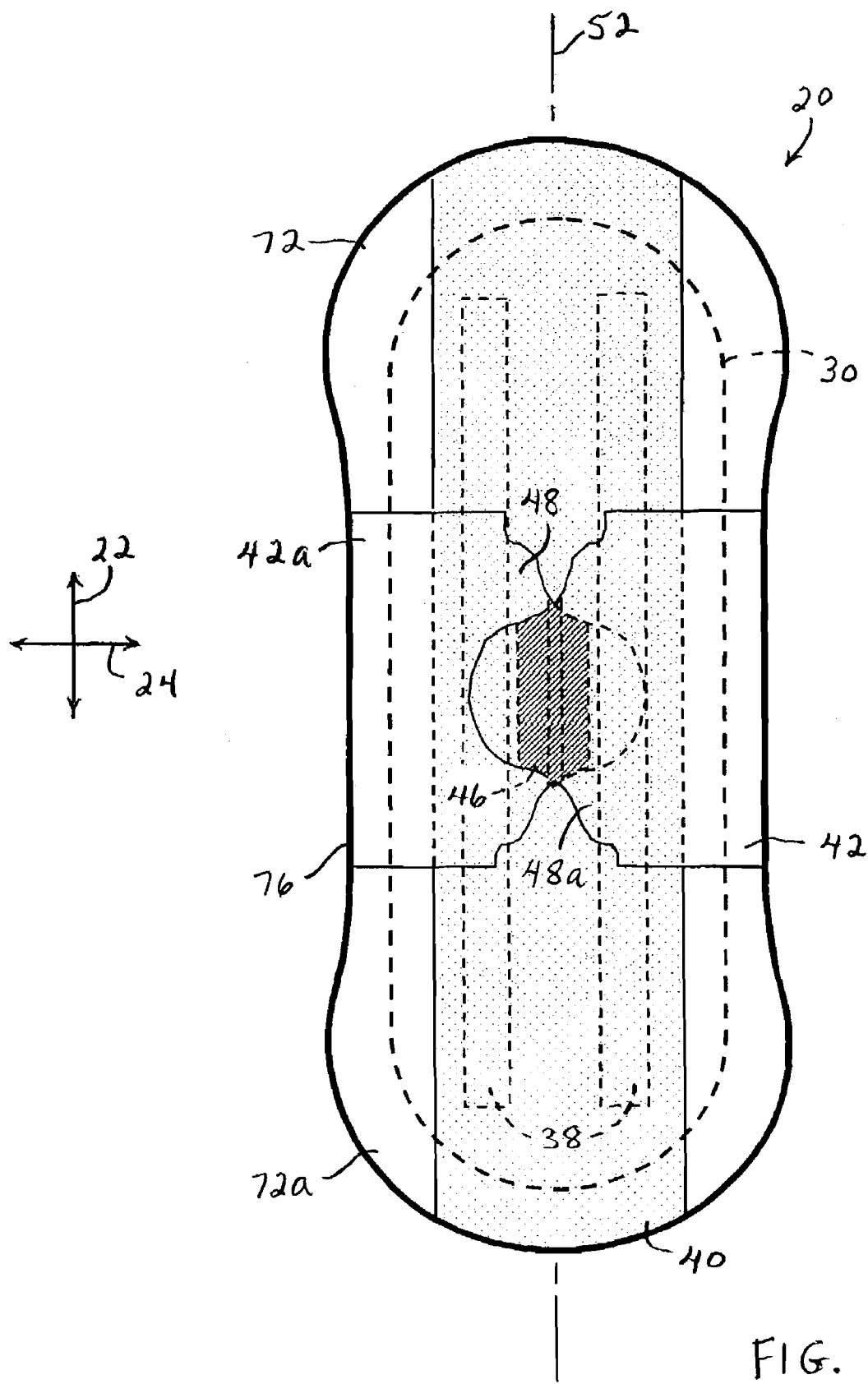
FIG. 1A shows a representative, bottom, plan view of a bodyside of the absorbent article illustrated in FIG. 1.
Figure 1B:
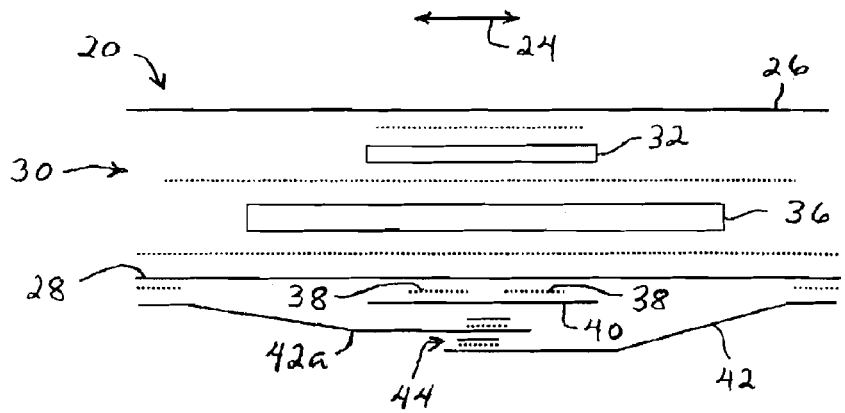
FIG. 1B shows an expanded, schematic view of a representative, transverse cross-section of the absorbent article illustrated in FIG. 1.
Figure 1C:
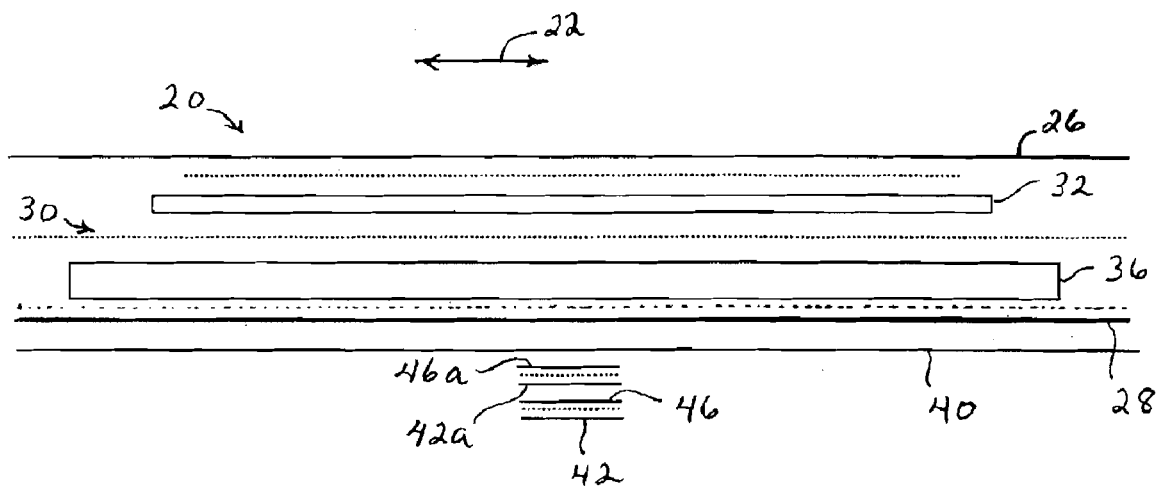
FIG. 1C shows an expanded, schematic view of a representative, longitudinal cross-section of the absorbent article illustrated in FIG. 1.

FIGS. 1 through 1C, illustrate an example of a suitable article, such as the representatively shown feminine care article, which is configured to incorporate the present invention. The feminine care article can, for example, be a feminine care pad or napkin 20, and the article can have a lengthwise longitudinal direction 22, a transverse, laterally extending, cross-direction 24, first and second longitudinally opposed end portions 72 and 72a, and an intermediate portion 76 located between the end portions. As representatively shown, the longitudinal dimension of the article is relatively larger than the lateral dimension of the article. The article 20 can include a topsheet or cover 26, a backsheet (also referred to herein as a baffle) 28, and an absorbent structure 30 positioned between the cover and baffle. In a particular aspect, the absorbent structure 30 can at least include an intake layer 32 and a shaping layer 36. In other aspects, the intake and shaping layers can have configurations of absorbent capacities, configurations of densities, configurations of basis weights and/or configurations of sizes which are selectively constructed and arranged to provide desired combinations of liquid intake time, absorbent saturation capacity, absorbent retention capacity, z-directional liquid distribution along the thickness dimension of the article, shape maintenance, and aesthetics.

The cover 26 may include a layer constructed of any operative material, and may be a composite material. For example, the cover layer can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded-web, a bicomponent spunbond fabric or the like as well as combinations thereof. For example, the cover layer can include a woven fabric, a nonwoven fabric, a polymeric film that has been configured to be operatively liquid-permeable, or the like, as well as combinations thereof. Other examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A more particular example of a suitable cover layer material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a non-woven fabric material. The composite materials are typically in the form of integral sheets generally formed by the extrusion of a polymer onto a web of spunbond material. In a desired arrangement, the cover layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the cover layer. The apertures or other openings can help increase the rate at which bodily liquids can move through the thickness of the cover layer and penetrate into the other components of the article (e.g. into the absorbent structure 30). The selected arrangement of liquid-permeability is desirably present at least on an operative portion of the cover layer that is appointed for placement on the body-side of the article. The cover layer 26 can provide comfort and conformability, and can function to direct bodily exudates away from the body and toward the absorbent structure 30. In a desired feature, the cover layer 26 can be configured to retain little or no liquid in its structure, and can be configured to provide a relatively comfortable and non-irritating surface next to the body-tissues of a female wearer. The cover layer 26 can be constructed of any material which is also easily penetrated by bodily fluids that contact the surface of the cover layer.

The cover 26 may be maintained in secured relation with the absorbent structure 30 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 26 typically extends over the upper, bodyside surface of the absorbent structure, but can alternatively extend around the article to partially or entirely, surround or enclose the absorbent structure. Alternatively, the cover 26 and the baffle 28 can have peripheral margins which extend outwardly beyond the terminal, peripheral edges of the absorbent structure 30, and the extending margins can be joined together to partially or entirely, surround or enclose the absorbent structure.

The baffle 28 may include a layer constructed of any operative material, and may or may not have a selected level of liquid-permeability or liquid-impermeability, as desired. In a particular configuration, the backsheet or baffle 28 may be configured to provide an operatively liquid-impermeable baffle structure. The baffle may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Desirably, the baffle 28 can operatively permit a sufficient passage of air and moisture vapor out of the article, particularly out of an absorbent (e.g. storage or absorbent structure 30) while blocking the passage of bodily liquids. An example of a suitable baffle material can include a breathable, microporous film, such as a HANJIN Breathable Baffle available from Hanjin Printing, Hanjin P&C Company Limited, a business having offices located in Sahvon-li.Jungan-mvu.Kongiu-City, Chung cheong nam-do, Republic of South Korea. The baffle material is a breathable film, which is white in color, dimple embossed and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable baffle material can include a closed cell polyolefin foam. For example, a closed cell polyethylene foam may be employed. Still another example of a baffle material would be a material that is similar to a polyethylene film which is used on commercially sold KOTEX brand pantiliners, and is obtainable from Pliant Corporation, a business having offices located in Schaumburg, Ill., USA.

The structure of the absorbent body 30 can be operatively configured to provide a desired level of absorbency or storage capacity. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural and/or synthetic fiber.

The absorbent structure 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. saline with 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc. The superabsorbent material may desirably be included in an appointed storage or retention portion of the absorbent system, and may optionally be employed in other components or portions of the absorbent article.

As representatively shown, the absorbent body 30 of the selected article can comprise a composite structure having a selected plurality of strata or layers. With reference to FIGS.

1 through 1C, for example, the absorbent composite can include an intake layer 32 and an absorbent shaping layer 36, as well as any other desired components, arranged in any operative combination. As representatively shown, the structure of the absorbent body can include an absorbent pad, shaping layer 36 which is positioned between the cover 26 and the baffle 28, and can include an intake layer 32 which is positioned between the cover 26 and the shaping layer 36.

In a particular aspect, the article 20 can include a top, bodyside intake layer 32 which is sized and placed to more effectively operate in a target area of the absorbent body 30 where liquids are more likely to be introduced into the article. The material of the intake layer can be configured to provide desired liquid-intake properties, substantially without consideration for delivering shaping properties. For example, the configuration of the intake layer need not include properties that are configured to prevent bunching and twisting of the article, particularly the absorbent structure, during ordinary wear.

The intake layer can include material that is configured to quickly absorb and pull liquid away from the body. Accordingly, the intake layer 32 can provide the function of liquid intake and can also provide the functions of liquid distribution, spreading, temporary storage and liquid retention. The intake layer may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the absorbent body may include one or more components that can modify menses or intermenstrual liquid.

In a particular arrangement, the intake layer can be a thermally-bonded, stabilized airlaid fibrous web (e.g. Concert code 175.1020) available from Concert Fabrication, a business having offices located in Gatineaux, Quebec, Canada. The intake layer may optionally be provided by a similar, stabilized airlaid fibrous web available from Buckeye Technologies, Inc., a business having offices located in Memphis, Tenn., U.S.A.

In a desired feature, the intake layer 32 can have a relatively lower basis weight, as compared to the bottom (garment-side) retention/shaping layer 36. Optionally, the basis weight of the intake layer may be equal or similar to the basis weight of the shaping layer. In another feature, the intake layer 32 can have a lower density (e.g., be more lofty), as compared to the retention/shaping layer 36.

In a particular aspect, the basis weight of the intake layer 32 can be at least a minimum of about 30 g/m² The basis weight of the intake layer can alternatively be at least about 100 g/m², and can optionally be at least about 120 g/m² to provide improved performance. In other aspects, the basis weight of the intake layer can be up to a maximum of about 250 g/m², or more. The basis weight of the intake layer can alternatively be up to about 200 g/m², and can optionally be up to about 175 g/m² to provide improved effectiveness.

In another aspect, the density of the intake layer 32 can be at least a minimum of about 0.01 g/cm³. The intake layer density can alternatively be at least about 0.02 g/cm³, and can optionally be at least about 0.04 g/cm³ to provide improved performance. In still other aspects, the intake layer density can be up to a maximum of about 0.1 g/cm³, or more. The intake layer density can alternatively be up to about 0.09 g/cm³, and can optionally be up to about 0.08 g/cm³ to provide improved effectiveness. In a desired arrangement, the density of the intake layer can be about 0.06 g/cm³.

A particular feature can include an intake layer 32 which includes fibers that can provide an intake layer that is relatively more "hydrophilic" than the shaping layer 36. Still another feature can include an intake layer wherein at least an operative portion of the fibers have been semi-treated by incorporating a debonding agent to improve opening and fiberization during the manufacturing process. Other suitable intake layer properties are described in U.S. Patent Application No. 2004/0186448.

Figure 5:
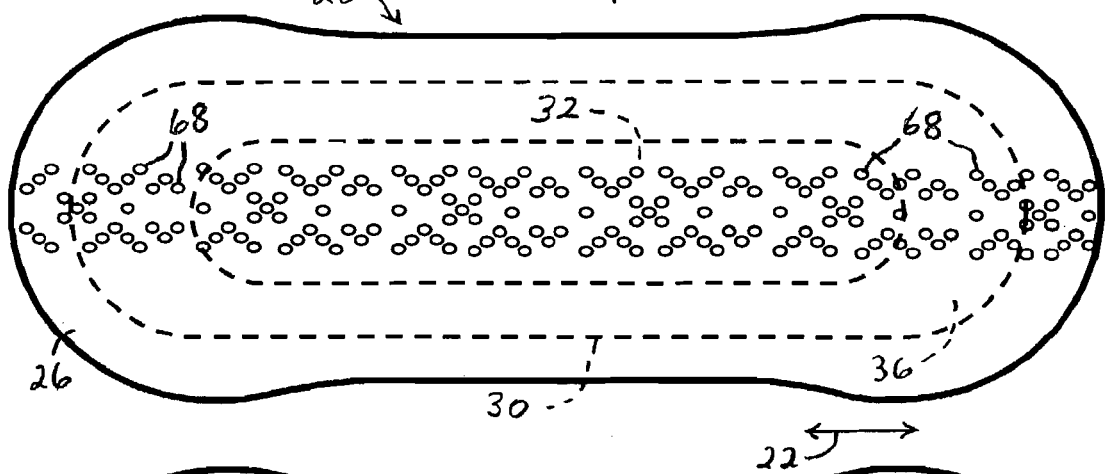
FIG. 5 shows a representative, top view of a bodyside of an absorbent article having a selected pattern of apertures formed into the bodyside surface of the article.
Figure 5A:
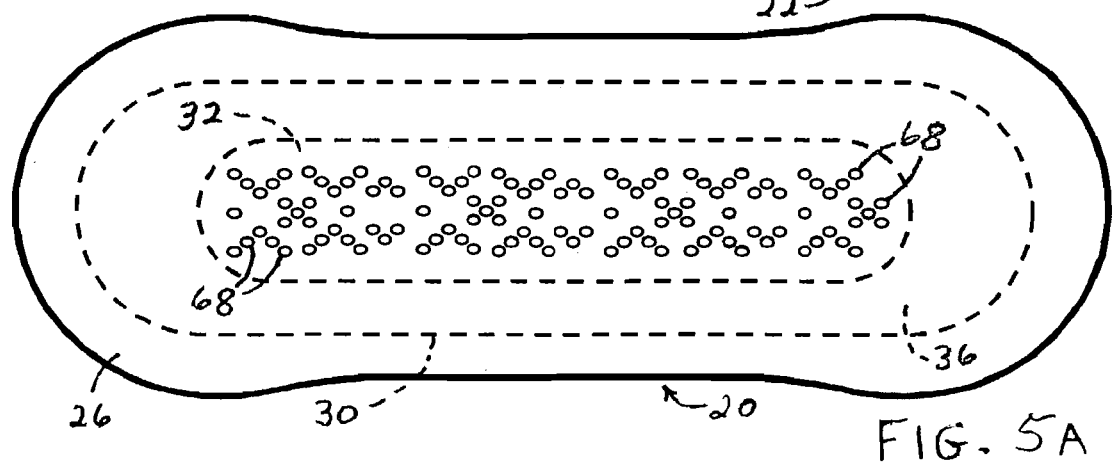
FIG. 5A shows a representative, top view of a bodyside of an absorbent article having another distribution of apertures formed into the bodyside surface of the article.
Figure 5B:
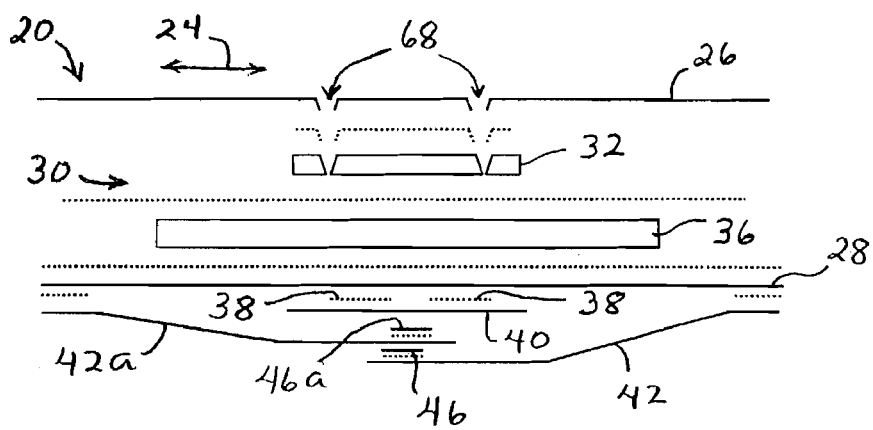
FIG. 5B shows a schematic, expanded view of a representative, transverse cross-section of the absorbent article illustrated in FIG. 5.

The top intake layer 32 may have any operative shape and/or design. For example, the intake layer may include a single piece of material, or multiple pieces of material, such as multiple strips of material. In addition, the intake layer 32 may include holes or apertures 68 (e.g. FIGS. 5 through 5B) to better provide desired liquid-intake properties. The apertures may extend partially or completely through the z-directional thickness of the intake layer 32, as desired.

The shaping layer 36 can provide the functions of liquid storage and retention, liquid distribution, liquid spreading and shape maintenance. The shaping layer may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the shaping layer may include one or more components that can modify the menses or intermenstrual liquid.

In a particular arrangement, the shaping layer can be a thermally-bonded, stabilized airlaid fibrous web available from Concert Fabrication (Concert code 225.1021), a business having offices located in Gatineaux, Quebec, Canada (e.g. Concert code 225.1021). The shaping layer 36 may optionally be provided by a similar, stabilized airlaid fibrous web available from Buckeye Technologies, Inc., a business having offices located in Memphis, Tenn., U.S.A.

The shaping layer can have a higher basis weight, as compared to the intake layer 32, but may optionally have a similar or equal basis weight. In another feature, the density of the retention/shaping layer 36 can be greater than that of the intake layer 32, and may include a density gradient through the material of the intake layer (e.g. with higher densities positioned relatively closer to the bottom, garment-side of the article). The equal or greater basis weight and higher density of the shaping layer 36 can result in a relatively stiffer material in the bottom retention/shaping layer 36, as compared to the top intake layer 32. The configuration of the shaping layer 36 can better promote liquid transfer to the baffle-side of the article, away from the wearer's skin, and can decrease the likelihood of liquid rewet or flowback to the wearer's skin. Additionally, the shaping layer configuration can reduce the amounts of saturation capacity and retention capacity that are needed to provide a consumer-preferred product.

In a particular aspect, the basis weight of the shaping layer 36 can be at least a minimum of about 100 g/m². The shaping layer basis weight can alternatively be at least about 130 g/m², and can optionally be at least about 165 g/m² to provide improved performance. In other aspects, the basis weight of the shaping layer can be up to a maximum of about 400 g/m², or more. The shaping layer basis weight can alternatively be up to about 350 g/m², and can optionally be up to about 325 g/m² to provide improved effectiveness. In a desired configuration, the shaping layer basis weight can be about 225 g/m².

In a further aspect, the density of the shaping layer 36 can be at least a minimum of about 0.06 g/cm³. The shaping layer density can alternatively be at least about 0.07 g/cm³, and can optionally be at least about 0.08 g/cm³ to provide improved performance. In other aspects, the density of the shaping layer can be up to a maximum of about 0.3 g/cm³, or more. The shaping layer density can alternatively be up to about 0.2 g/cm³, and can optionally be up to about 0.16 g/cm³ to provide improved effectiveness. In a desired arrangement, the density of the shaping layer 36 can be about 0.12 g/cm³. Other suitable properties of shaping layer materials are described in U.S. Patent Application No. 2004/0186448.

Figure 4:
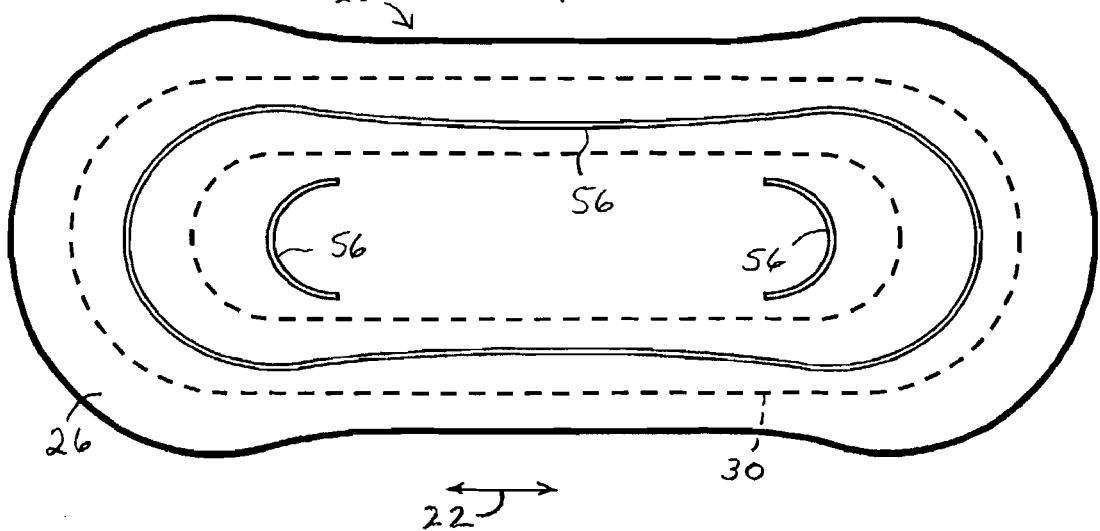
FIG. 4 shows a representative, top view of a bodyside of an absorbent article having a selected pattern of embossments formed into the article.
Figure 4A:
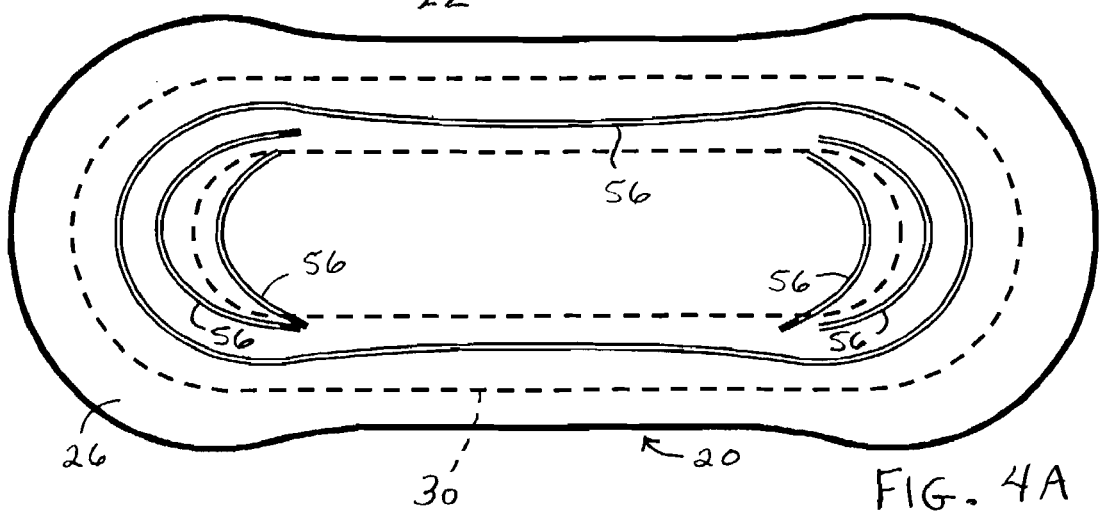
FIG. 4A shows a representative, top view of a bodyside of an absorbent article having another distribution of embossments formed into the article.
Figure 4B:
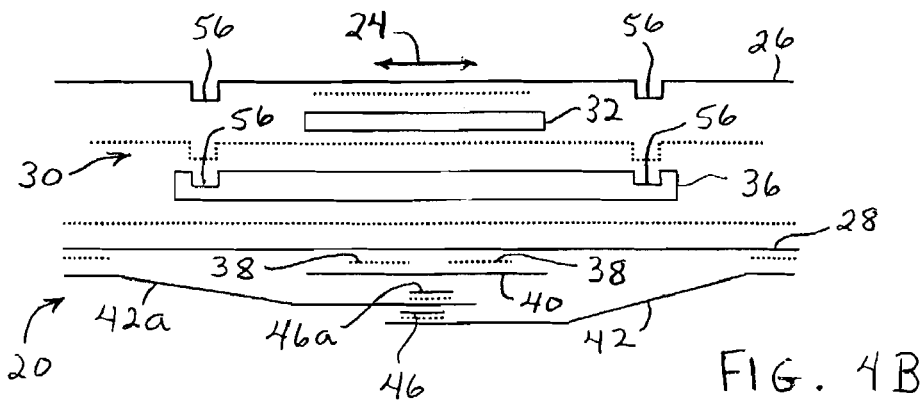
FIG. 4B shows an expanded, schematic view of a representative, transverse cross-section of the absorbent article illustrated in FIG. 4.

In optional arrangements, the article 20 may include additional components or component layers, as desired. For example, a transfer layer may be positioned between the intake layer 32 and the shaping layer 36. In another feature, the article may include any desired pattern of embossments 56 (e.g. FIGS. 4 through 4B) formed into at least the bodyside surface of the article. The embossing can deform the bodyside of the cover and can deform selected portions of the absorbent body 30 to provide operative channel regions that can help block, direct or otherwise control a desired movement of liquids along the bodyside surface of the article. The embossing can also provide an aesthetic benefit to the consumer, and a visual cue regarding fit and leakage protection. In particular arrangements, the embossments can be positioned generally adjacent the perimeter edges of the absorbent body 30. In other aspects, the embossments can be configured to provide a regular or irregular pattern having one or more channels which are distributed in a symmetrical or asymmetrical array, as desired.

The article 20 can include a system of side-panel or wing portions 42 which can be integrally connected to appointed sections of the side regions 60 along the intermediate portion of the article. For example, the side-panels or wings can be separately provided members that are subsequently attached or otherwise operatively joined to the intermediate portion of the article 20 (e.g. FIGS. 1 through 1C).

Figure 2:
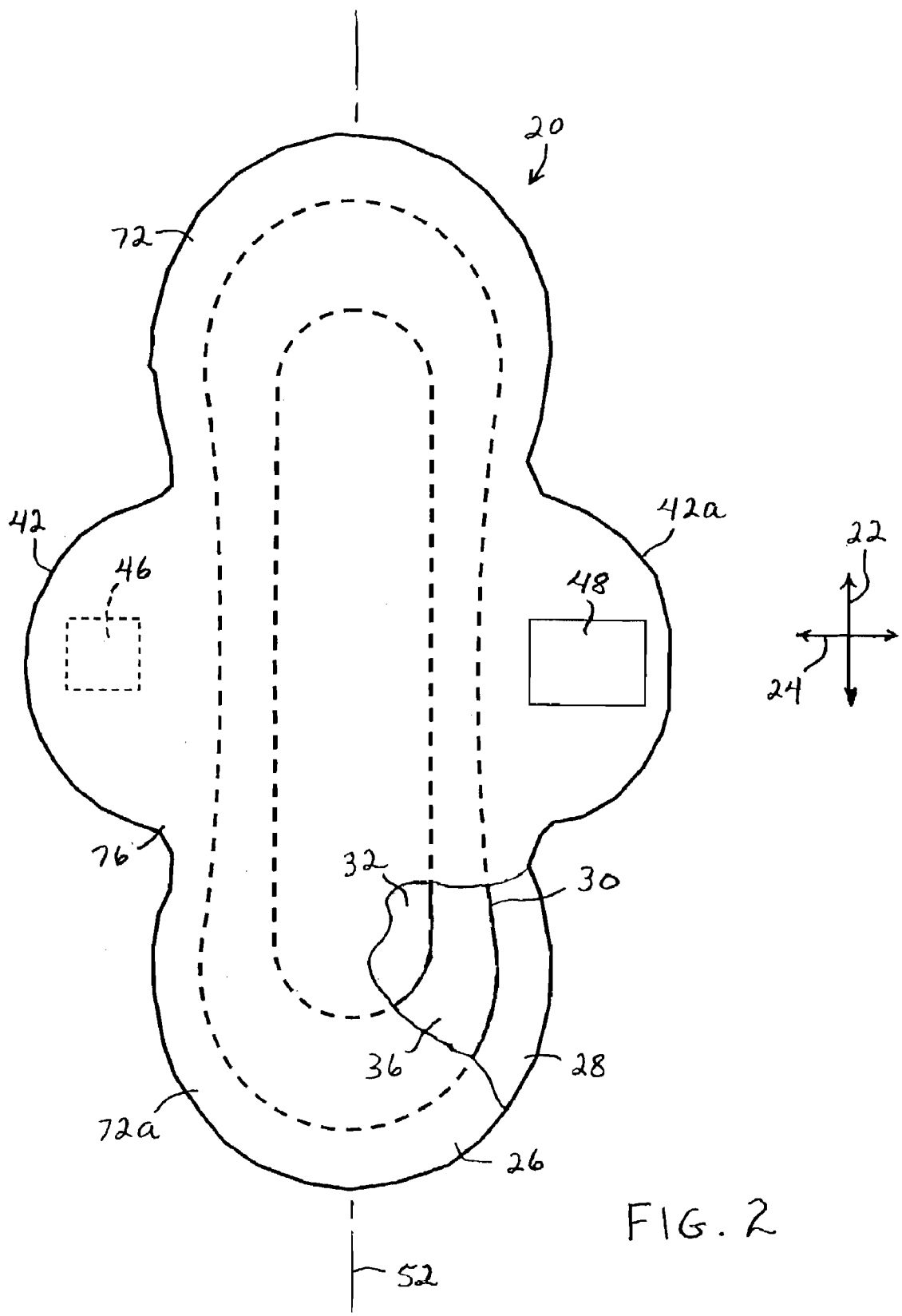
FIG. 2 shows a representative, partially cut-away, top, plan view of a bodyside of an absorbent article having side-panels or wings that have been unitarily formed with one or more components of the article, where the wings include a system of interengaging mechanical fasteners.

In other configurations, the wings or side-panels 42 can be unitarily formed with one or more components of the article. As representatively shown in FIGS. 2 through 3C, for example, either or both wing portions may be formed from a corresponding, operative extension of the material employed to form the cover 26. Alternatively, either or both wing portions may be formed from a corresponding, operative extension of the material employed to form the baffle 28, or formed from a corresponding, operative combination of the cover and baffle materials.

Figure 2A:
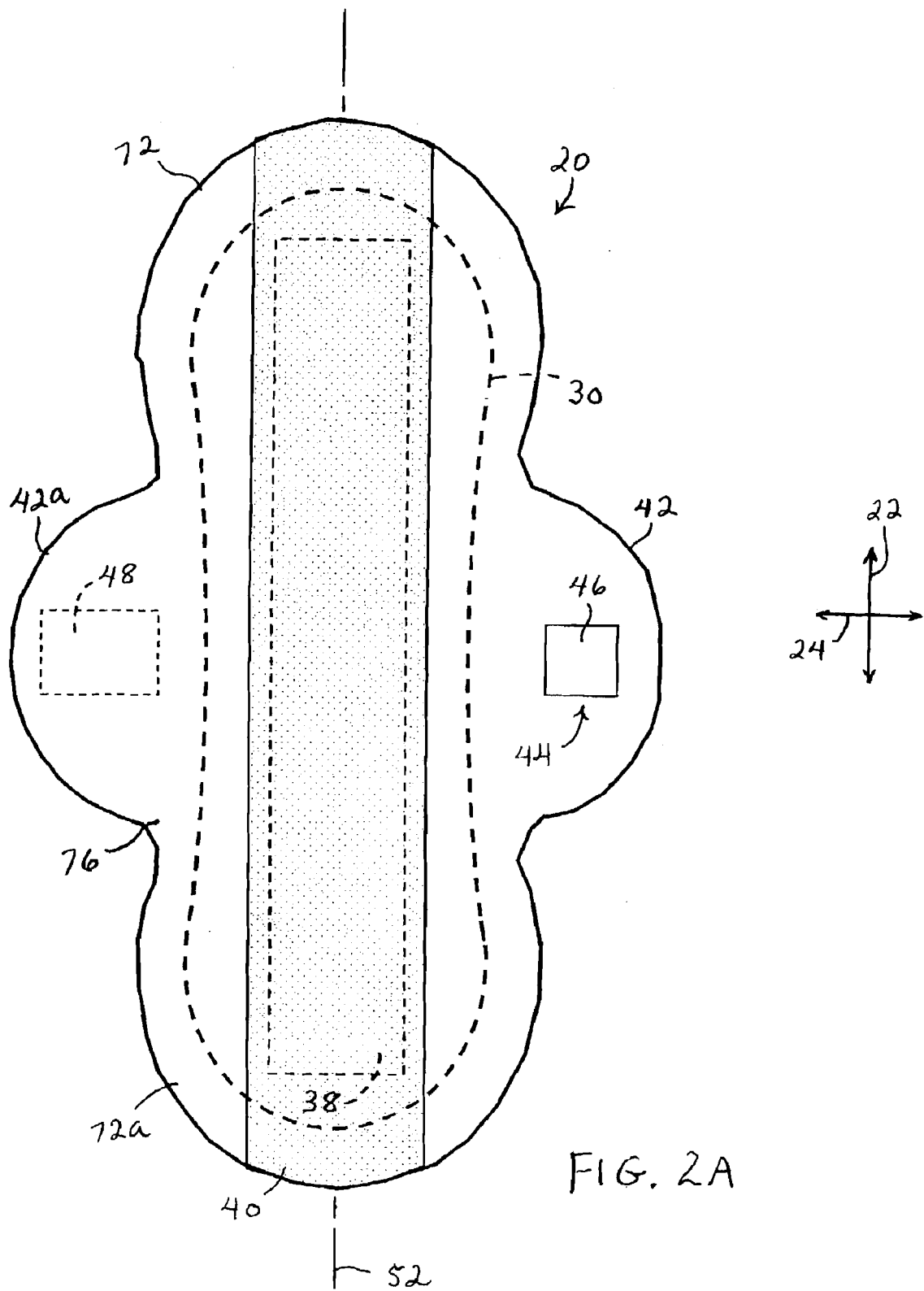
FIG. 2A shows a representative, bottom, plan view of a garment-side of the absorbent article illustrated in FIG. 2.
Figure 2B:
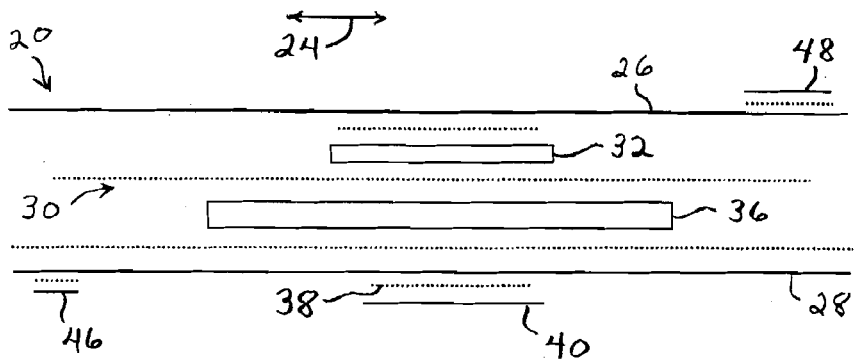
FIG. 2B shows an expanded, schematic view of a representative, transverse cross-section of the absorbent article illustrated in FIG. 2.
Figure 2C:
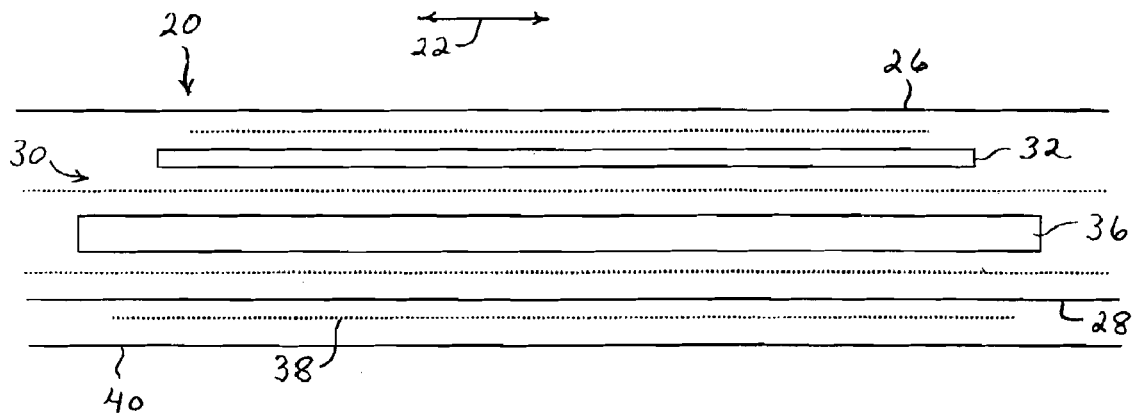
FIG. 2C shows an expanded, schematic view of a representative, longitudinal cross-section of the absorbent article illustrated in FIG. 2.

The side-panels can have an appointed storage position (e.g. FIGS. 1A through 1C) in which the side-panels 42 are directed generally inwardly toward the longitudinally-extending centerline 52. As illustrated, the side-panel that is connected to one side margin may have sufficient cross-directional length to extend and continue past the centerline 52 to approach the laterally opposite side margin of the article. The storage position of the side-panels can ordinarily represent an arrangement observed when article is first removed from its wrapper or other packaging. Prior to placing the article into a bodyside of an undergarment prior to use, the side-panels 42 can be selectively arranged to extend laterally from the side regions 60 of the article intermediate portion (e.g. FIGS. 2 and 2A). After placing the article in the undergarment, the side-panels 42 can be operatively wrapped and secured around the side edges of the undergarment to help hold the article in place.

Additionally, a selected configuration of garment adhesive 38, such as the illustrated strip regions, may be distributed onto the garment-side of the article to help secure the article to the undergarment. Typically, the garment adhesive can be distributed over the garment-side of the baffle, and one or more layers or sheets of release material 40 can be removably placed over the garment adhesive during storage prior to use.

The side-panel portions 42 can have any operative construction, and can include a layer of any operative material.

Additionally, each side-panel can comprise a composite material. For example, the side-panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Each side-panel 42 can be joined to its corresponding side region 60 of the article in any operative manner. For example, the side-panel can be joined to the cover 26, the baffle 28 or another article component, as well as any combination thereof. In the illustrated example, each side-panel 42 is joined to the outward, garment-side surface of the baffle 28, but may optionally be joined to the bodyside surface of the baffle. The side-panel can be attached with hotmelt adhesive, but any other operative adhesive or attachment mechanism may alternatively be employed.

In another feature, each side-panel portion 42, or any desired combination of the employed side-panel portions, can include a panel-fastener component 44 which is operatively joined to an appointed engagement surface of its associated side-panel. The panel-fastener can be configured to operatively attach to the wearer's undergarment and/or to any appointed, landing-zone portion of the article 20. For example, the panel-fastener can include a system of interengaging mechanical fasteners, a system of adhesive fasteners, a system of cohesive fasteners or the like, as well as combinations thereof.

With reference to FIGS. 1A through 2C, for example, either or both side-panels 42 can include a hook or other "male" component 46 of an interengaging mechanical fastener system. Any operative hook component may be employed. For example, a suitable hook component materials can include a J-hook, mushroom-head hook, flat-top nail-head hook, a palm-tree hook, a multiple-J hook or the like, as well as combinations thereof.

Figure 3:
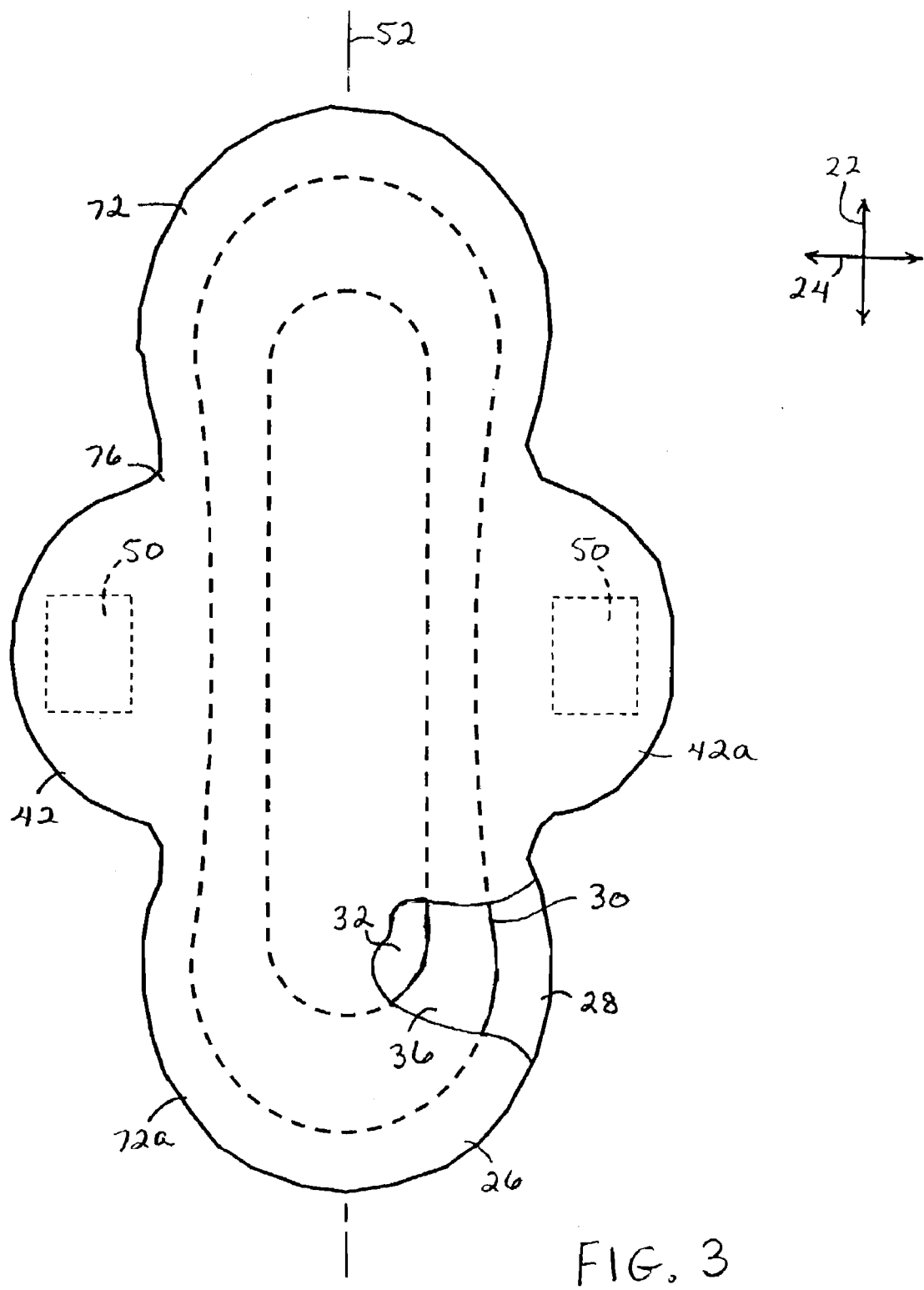
FIG. 3 shows a representative, partially cut-away, top, plan view of a bodyside of an absorbent article having side-panels or wings that have been unitarily formed with one or more components of the article, where the wings include a system of adhesive fasteners.
Figure 3A:
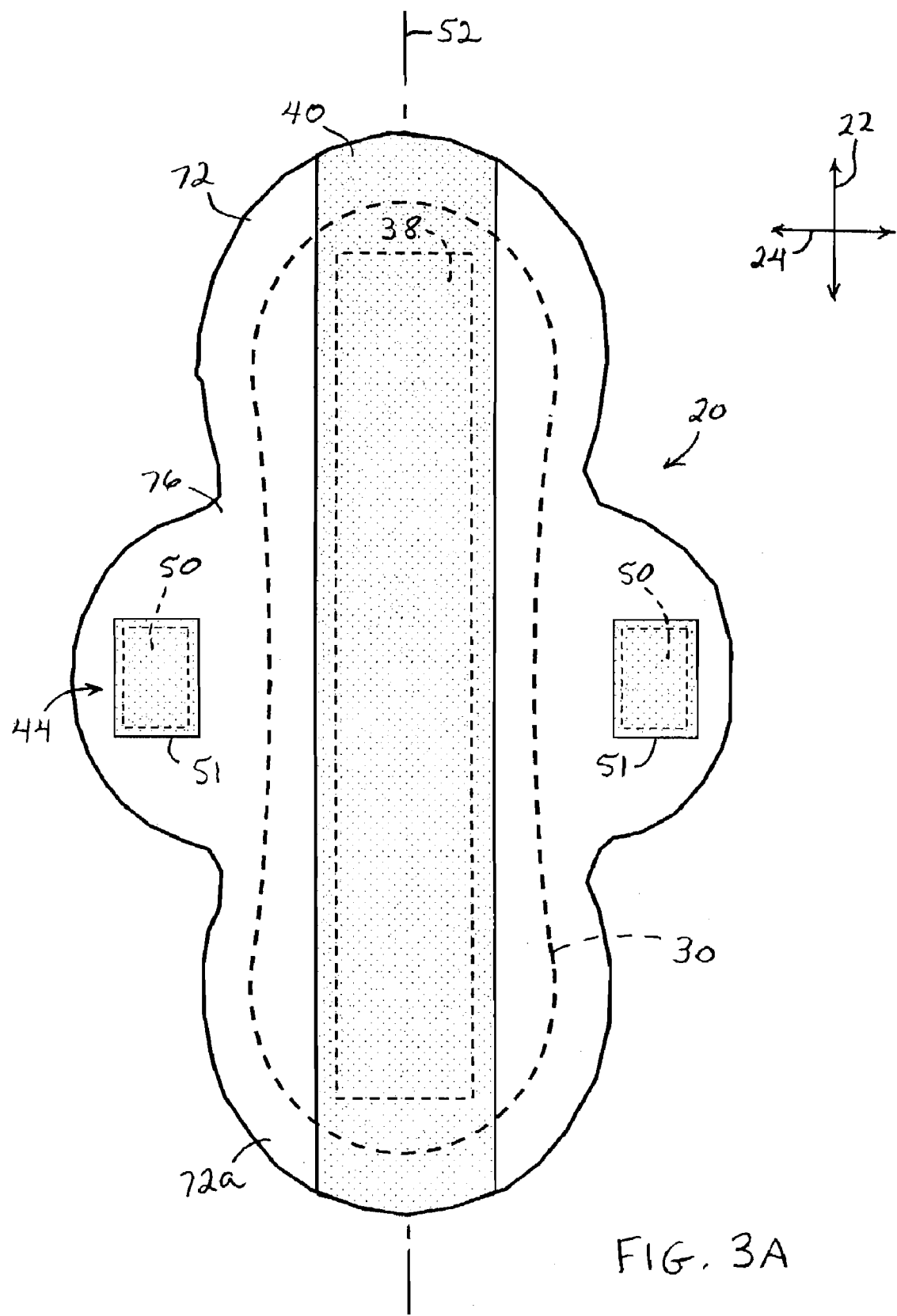
FIG. 3A shows a representative, bottom, plan view of a garment-side of the absorbent article illustrated in FIG. 3.
Figure 3B:
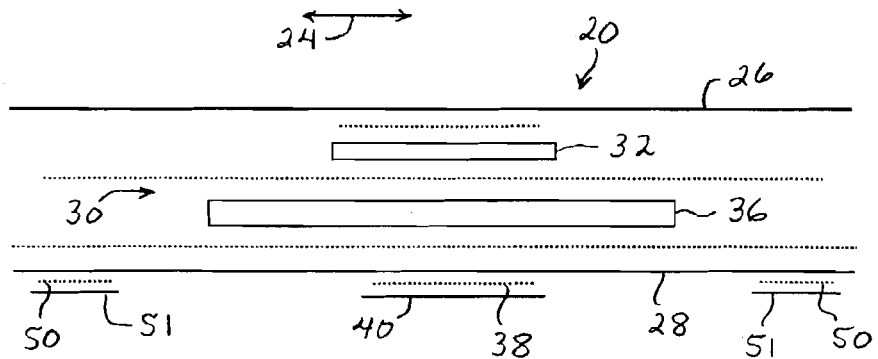
FIG. 3B shows an expanded, schematic view of a representative, transverse cross-section of the absorbent article illustrated in FIG. 3.
Figure 3C:
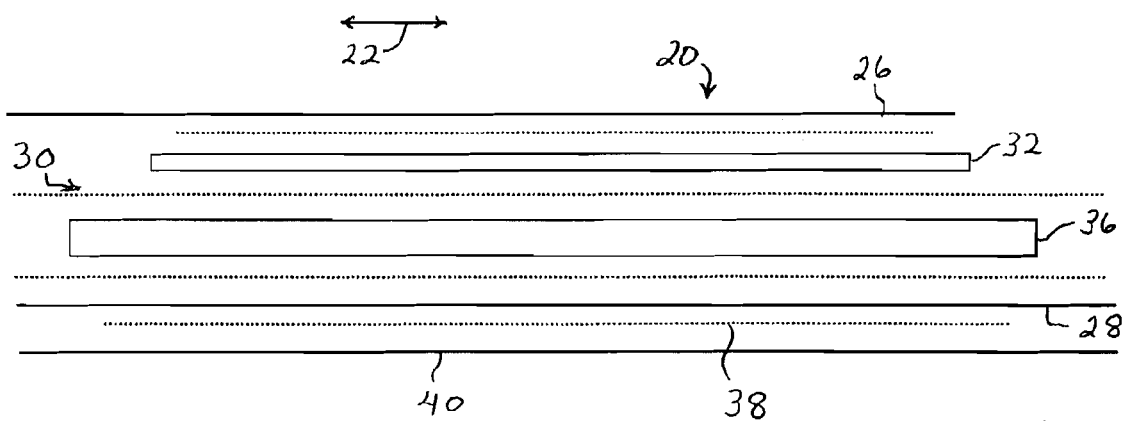
FIG. 3C shows an expanded, schematic view of a representative, longitudinal cross-section of the absorbent article illustrated in FIG. 3.

With reference to FIGS. 3 through 3C, for example, either or both side-panels 42 can include a panel-fastener system 44 which alternatively incorporates an operative adhesive 50. The adhesive may be a solvent-base adhesive, a hotmelt adhesive, a pressure-sensitive adhesive, or the like, as well as combinations thereof. Each section of adhesive 50 may be covered with a removable release sheet 51.

An operative first section of the selected hook component 46 can be joined to a major facing surface of at least a first side-panel portion 42, and can be configured to contact or otherwise engage a cooperating loop material 48 provided on a second side-panel portion 42a during ordinary use, as representatively shown in FIGS. 1A and 1B. Additionally, an operative second section of a hook component 46a, composed of the same or different type of hook material, can be joined to a major facing surface of the second side-panel portion 42a, and can be configured to contact or otherwise engage an outward surface of the wearer's undergarment during ordinary use. For example, the hook component can be arranged to operatively engage and removably attach to the outward surface of a crotch region of the undergarment.

Each side-panel portion 42, or any desired combination of the employed side-panel portions, can include a loop or other "female" component 48 of an interengaging mechanical fastener system. Any operative loop component may be employed. For example, a suitable loop component material can include a woven fabric, a knit fabric, a nonwoven fabric, a fabric laminated to a substrate or the like, as well as combinations thereof. The loop material may be integrally formed with or otherwise provided by the material of its corresponding side-panel portion. Optionally, the loop material may be a separately provided component of that is subsequently assembled to its corresponding side-panel portion.

An operative first section of a selected loop component 48 can be joined to a major facing surface of at least the second side-panel portion 42a, and can be configured to contact or otherwise engage the hook component 46 on the first side-panel portion 42 during ordinary use, as representatively shown in FIGS. 1A and 1B. Additionally, an operative second section of a loop component 48a, composed of the same or different type of loop material, can be joined to a major facing surface of the first side-panel portion 42. As a result, the user can have the option of alternatively attaching the second hook component 46a of the second side-panel onto the second loop component 48a of the first side-panel. Accordingly, the first hook component 46 may alternatively be engaged with the outward surface of the wearer's undergarment.

Each or any desired combination of the provided loop components (48, 48a) may be a separately provided member that is subsequently joined and assembled to its corresponding side-panel portion (42a, 42). In a desired feature, each or any desired combination of the provided loop components can be integrally provided by the material employed to construct its corresponding side-panel portion.

In the various arrangements of the present invention, the hook component 46 can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$), and can optionally be at least about 3000 hooks/in$^2$ (about 465 hooks/cm$^2$) to provide improved performance. In another aspect, the hook density can be not more than a maximum of about 7000 hooks/in$^2$ (about 1085 hooks/cm$^2$). The hook density can alternatively be not more than about 6000 hooks/in$^2$ (about 930 hooks/cm$^2$), and can optionally be not more than about 5000 hooks/in$^2$ (about 775 hooks/cm$^2$) to provide improved performance.

Examples of suitable hook materials can include 85-Series and 61-Series hook materials available from Velcro, U.S.A., a business having offices located in Manchester, N.H., U.S.A. The hook materials can have a hook density of about 775 hooks/cm$^2$.

In a particular aspect, the material of the loop component 48 may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515, the entire disclosure of which is incorporated herein by reference in a manner that is consistent herewith.

DEFINITIONS

As used herein the term "viscoelastic" means a composition having at least one significant component that is moderately viscous and has elastic properties. By "moderately viscous" it is meant that the component has a viscosity of at least that of normal human blood plasma. By "elastic" it is meant that the component has elasticity equal to or greater than normal human blood plasma.

As used herein, the term "viscoelastant" means an organic agent that, when an effective amount is contacted by a viscoelastic composition, materially alters the properties of that viscoelastic composition, for example, by reducing its viscosity and/or elastic nature. By "materially alters" it is meant that the property measured as described is changed by at least a statistically significant amount and, advantageously, this change will be at least about 30% for many applications.

As used herein the term "nonwoven fabric or web" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times$ 0.89×0.00707=1.415). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly dispersed meltblown fibers. Such a process is disclosed, for example, in U.S. Pat. No. 3,849,241 to Butin. Meltblown fibers are microfibers which may be continuous or discontinuous and are generally smaller than 10 microns in average diameter.

As used herein "bonded carded webs" or "BCW" refers to nonwoven webs formed by carding processes as are known to those skilled in the art and further described, for example, in coassigned U.S. Pat. No. 4,488,928 to Alikhan and Schmidt which is incorporated herein in its entirety by reference. Briefly, carding processes involve starting with a blend of, for example, staple fibers with bonding fibers or other bonding components in a bulky batt that is combed or otherwise treated to provide a generally uniform basis weight. This web is heated or otherwise treated to activate the adhesive component resulting in an integrated, usually lofty nonwoven material.

As used here, "airlaid" refers to nonwovens formed by airlaying processes. "Airlaying" is a well-known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive. Airlaying is taught in, for example, U.S. Pat. No. 4,640,810 to Laursen et al.

As used herein, "coform" is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives, e.g. titanium dioxide for color, are generally present in an amount less than 5 weight percent and more typically about 2 weight percent.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

As used herein the term "blend" as applied to polymers, means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, through air bonding or "TAB" means a process of bonding a nonwoven, for example, a bicomponent fiber web in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provide the bonding. Through air bonding has restricted variability and is often regarded a second step bonding process. Since TAB requires the melting of at least one component to accomplish bonding, it is restricted to webs with two components such as bicomponent fiber webs or webs containing an adhesive fiber, powder or the like. TAB is frequently used to bond BCW materials.

As used herein "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g. like a window screen. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

EXAMPLES

The following non-limiting examples are provided to further illustrate the present disclosure.

Test Procedures

Unless otherwise indicated, the following procedures were used in the Examples described herein.

Menses Simulant Preparation: The viscoelastic fluid used in the examples described herein is a menses simulant designed to simulate the viscoelastic and other properties of menses. The menses simulant was prepared using a batch method based on the single bag simulant preparation method described in U.S. Pat. No. 5,883,231. As in the original method, the fluid is a combination of blood plasma, egg white, and red blood cells in a volume ratio of 3:4:3, respectively. The following procedure was used to prepare the menses simulant:

Swine blood was collected at an abattoir in plastic bottles and defibrinated (i.e., the fibrinogen and fibrin removed) by capping the bottles and shaking for approximately 5 minutes and then removing the resultant fibrin clots by mechanical separation. The resultant defibrinated blood was pooled, and the red blood cell and plasma components were separated by centrifuging the pooled blood at 3000 rpm for 60 minutes in a Sorvall Model RT6000D, using a swinging bucket rotor and 250 mL centrifuge bottles. Post centrifugation, the upper plasma layers were removed from the bottles and stored separately, the buffy coats (a thin layer of white blood cells and platelets that separated the upper plasma layer from the lower packed red blood cells) were removed and discarded, and the packed red blood cells were pooled and stored separately as well.

Egg whites were collected, with the egg yolks and chalazae removed, from four dozen fresh, jumbo chicken eggs. The thick egg white component was then separated from the whole egg white by straining the egg whites through a 2 mm plastic mesh. The thin egg white passed through the mesh, leaving the thick egg white, which was retained on the mesh, collected and stored.

The blood plasma and thick egg white were then blended by placing 1 liter of the thick egg white and 750 mL of blood plasma in a 2 liter, round-bottom reaction vessel and stirring the mixture for 3 hours at 1000 rpm using a disk-shaped stirrer. The stirrer was a 3" diameter×¼" thick stainless steel disk mounted orthogonally to the end of a stainless steel rod.

The plasma/egg white mixture was then transferred to a 3 liter plastic beaker, 750 mL of packed red blood cell were added, and the mixture was mixed by gentle stirring with a spatula for 2 to 3 minutes. The resultant menses simulant can be used immediately or stored for up to one week at 5° C., if gentamicin is added at a concentration of 50 µg/mL.

Viscoelastic Properties. The viscosity and elasticity of the viscoelastic fluids were measured using a Vilastic III Capillary Rheometer (Vilastic Scientific, Inc., Austin, Tex.). The Vilastic III Capillary Rheometer measures shear-dependent viscoelasticity by subjecting a test fluid in a stainless steel capillary tube to an oscillatory stress at a set frequency. The size of the tube, the oscillatory frequency and the extent of fluid displacement can all be varied. A 1 mm diameter by 6 cm long capillary tube was used at a fixed frequency of 0.1 Hz. Temperature was maintained at 22° C. The viscous and elastic components of the fluid were measured at 10 exponentially spaced shear rates between $0.1\ s^{-1}$ and $10\ s^{-1}$. The values for the viscous and elastic components of the measured viscoelasticity were least-squares fit on a log-log scale (listed in the examples as "Viscosity" and "Elasticity") and reported for the shear rate of $1.0\ s^{-1}$.

Fouling

As noted above, fouling is a measure of the change in permeability of a fluid as it passes through a porous medium. Permeability is a material property describing the flow of a fluid through a porous medium. To quantify permeability, Darcy's Law states that permeability (K) is the proportionality constant that relates the flow rate of a fluid through a material to (i) the cross-sectional area and thickness of the material, (ii) the viscosity of the fluid, and (iii) the pressure drop across the material according to the following formula:

$$K=(Q*\mu*L)/(A*\Delta P)$$

wherein
Q=flow rate
µ=fluid viscosity
L=thickness of material
A=cross-sectional area
ΔP=pressure drop Permeability and fouling are measured using a device that allows fluid (with a known viscosity) maintained at a fixed height above the test sample (i.e., a fixed pressure drop), to pass through a porous fabric sample of known diameter and thickness. Such devices are available commercially, e.g., a Liquid Permeameter available from Porous Materials, Inc. (Ithaca, N.Y. 14850). The rate of fluid flow is measured by collecting the fluid exiting the device and recording the mass of the collected fluid as a function of time. For a material with no fouling, the rate of fluid flow through the material is constant as a function of time. For a material that exhibits fouling, the permeability decreases with time and the amount of fluid passed. Fouling is a measure of the rate of decline in the permeability of the material as a function of the volume of fluid which has passed through it. In practice, a least-square fit of the plot of permeability (K) vs. fluid volume (V) is obtained, and fouling is defined as the slope of that line at V=0. Permeability and fouling are dependent on the nature of both the material and the fluid.

Intake Time. The intake test was performed using an acrylic rate block. The rate block is 3 inches (76.2 mm) wide and 2.87 inches (72.9 mm) deep and has an overall height of 1.125 inches (28.6 mm) which includes a center area on the bottom of the rate block that projects farther from the main body of the rate block and has a height of 0.125 inches (3.2 mm) and a width of 0.886 inches (22.5 mm). The rate block has a capillary with an inside diameter of 0.186 inches (4.7 mm) that extends diagonally downward from one side to the center line at an angle of 21.8 degrees from the horizontal. The capillary may be made by drilling the appropriately sized hole from the side of the rate block at the proper angle beginning at a point 0.726 inches (18.4 mm) above the bottom of the rate block; provided, however, that the starting point of the drill hole in the side must be subsequently plugged so that test fluid will not escape there. The top hole has a diameter of 0.312 inches (7.9 mm), and a depth of 0.625 inches (15.9 mm) so that it intersects the capillary. The top hole is perpendicular to the top of the rate block and is centered 0.28 inches (7.1 mm) from the side. The top hole is the aperture into which a funnel is placed. The center hole is for the purpose of viewing the progression of the test fluid and is actually of an oval shape. The center hole is centered width-wise on the rate block and has a bottom hole width of 0.315 inches (8 mm) and length of 1.50 inches (38.1 mm) from center to center of 0.315 inch (8 mm) diameter semi-circles making up the ends of the oval. The oval enlarges in size above 0.44 inches (11.2 mm) from the bottom of the rate block, for ease of viewing, to a width of 0.395 inches (10 mm) and a length of 1.930 inches (49 mm). The top hole and center hole may also be made by drilling. The rate block used to perform the intake tests is described more fully in U.S. Pat. No. 6,838,590, herein incorporated by reference.

Example 1

Effect of PEG 600 Lauryl Ether and PEG 600 Monolaurate on the Viscosity and Elasticity of Menses Simulant In this example, the effect of polyethylene glycol 600 lauryl ether and polyethylene glycol 600 monolaurate on the viscosity and elasticity of a menses simulant was determined.

19.6 grams of menses simulant (prepared as described above) was weighed into a 30 mL beaker. 0.4 grams of liquid surfactant (either polyethylene glycol 600 lauryl ether or polyethylene glycol 600 monolaurate) was added dropwise to the menses simulant to yield a 2 wt % surfactant solution in simulant. A small magnetic stir bar (approximately 0.5 inches long) was placed in the solution and the solution was stirred at about 4 rpm for 20 minutes to thoroughly mix. During mixing, a circular piece of polyethylene sheet (1/16 inch thick by 1 1/8 inch diameter—the approximate inner diameter of the 30 mL beaker) was floated on top of the treated menses solution to protect the simulant from denaturation and hemolysis induced by the air/fluid interface.

The viscosity and elasticity of untreated menses simulant, menses simulant treated with polyethylene glycol 600 lauryl ether, and menses simulant treated with polyethylene glycol 600 monolaurate were tested using a Vilastic III Capillary Rheometer, under the conditions as described above. The results given in Table 1 are the average of three measurements.

TABLE 1

| Fluid Sample | Viscosity (centipoise, cP) | Elasticity (centipoise, cP) |
|---|---|---|
| Untreated menses simulant | 24.6 | 5.30 |
| Menses simulant + 2 wt. % PEG 600 lauryl ether | 6.4 | 1.25 |
| Menses simulant + 2 wt. % PEG 600 monolaurate | 7.0 | 0.48 |

As can be seen from these results, menses simulant treated with 2 wt. % PEG 600 lauryl ether or 2 wt. % PEG 600 monolaurate had significantly lower viscosity and elasticity as compared with untreated menses simulant.

Example 2

Effect of Polyethylene Glycol 600 Lauryl Ether and Glucopon on the Viscosity and Elasticity of Menses Simulant In this example, the effects of polyethylene glycol 600 lauryl ether and Glucopon 220 on the viscosity and elasticity of a menses simulant were compared.

To begin, stock solutions of Glucopon 220 and PEG 600 lauryl ether in phosphate buffered saline (PBS) (0.15 M sodium chloride and 0.01 M sodium phosphate; pH 7.2) were prepared at concentrations of 10 wt. %, 3 wt. % and 1 wt. %.

Treated menses simulant samples were prepared by adding each stock solution to menses simulant (prepared as described above) at 1 part stock solution plus 9 parts menses simulant by volume, in 30 mL beakers. The mixtures (total volume of 20 mL) were stirred with a magnetic stir bar for 10 minutes at a speed of approximately 4 rpm. Viscosity and elasitcity measurements were begun twenty minutes after addition of the Glucopon or PEG 600 lauryl ether stock solutions to the menses simulant. A menses simulant control sample was prepared in the same manner, except instead of surfactant stock solution, 1/10 volume of PBS was added to the menses simulant.

Viscoelasticity tests were conducted with a Vilastic III Capillary Rheometer, under the conditions as described above. Each sample was tested eight times, and the results given in Table 2 are the average of the eight tests. The percent change in viscosity and percent change in elasticity for each sample as compared to the menses simulant control is given in parentheses. The percent change in viscosity was determined by subtracting the viscosity of the treated sample from the viscosity of the untreated sample and dividing the difference by the viscosity of the untreated sample. Percent change in elasticity was calculated in a similar manner.

TABLE 2

| Sample | Viscosity (cP) | Elasticity (cP) |
|---|---|---|
| Menses simulant control | 24.8 | 6.7 |
| Simulant + 0.1 wt % Glucopon | 17.4 (−30%) | 3.6 (−46%) |
| Simulant + 0.3 wt % Glucopon | 13.6 (−45%) | 3.4 (−49%) |
| Simulant + 1.0 wt % Glucopon | 12.2 (−51%) | 3.1 (−54%) |
| Simulant + 0.1 wt % PEG 600 lauryl ether | 20.8 (−16%) | 4.0 (−40%) |
| Simulant + 0.3 wt % PEG 600 lauryl ether | 9.5 (−62%) | 2.5 (−63%) |
| Simulant + 1.0 wt % PEG 600 lauryl ether | 6.2 (−75%) | 2.2 (−67%) |

As can be seen from these results, both Glucopon and PEG 600 lauryl ether were effective at reducing the viscosity and elasticity of menses simulant at 0.1 wt. %, 0.3 wt. %, and 1.0 wt. % concentrations. At 0.1 wt. % concentration, Glucopon was slightly more effective than the PEG 600 lauryl ether at reducing viscosity and elasticity, while at the 0.3 wt. % and 1.0 wt. % concentrations the PEG 600 lauryl ether had a better effect on viscosity and elasticity than did Glucopon.

Example 3

Effect of Treatment Agents on Viscosity, Elasticity, and Fouling Effects of Menses Simulant In this example, the effects of various viscoelastant agents on the viscosity, elasticity, and fouling effects of a menses simulant were compared.

To begin, 99 grams of menses simulant (prepared as described above) was weighed into a 100 mL beaker. 1.0 grams of viscoelastant agent(s) (either sodium citrate, dextran, cysteine, polyethylene glycol 600 lauryl ether, polyethylene glycol 600 monolaurate, Glucopon 220, or equivalent amounts of sodium citrate and polyethylene glycol 600 monolaurate (i.e., 0.5 g sodium citrate and 0.5 g PEG 600 monolaurate)) was added to the menses simulant to yield 1 wt % viscoelastant agent(s) solution in simulant. A small magnetic stir bar (approximately 0.5 inches long) was placed in the solution and the solution was stirred at about 4 rpm for 20 minutes to thoroughly mix. During mixing, a piece of polyethylene sheet (approximately the inner diameter of the 100 mL beaker) was floated on top of the treated menses solution to protect the simulant from denaturation.

The viscosity and elasticity of untreated menses simulant, menses simulant treated with sodium citrate, menses simulant treated with dextran, menses simulant treated with cysteine, menses simulant treated with polyethylene glycol 600 lauryl ether, menses simulant treated with polyethylene glycol 600 monolaurate, menses simulant treated with Glucopon, and menses simulant treated with polyethylene glycol 600 monolaurate and sodium citrate was tested using a Vilastic III Capillary Rheometer, under the conditions as described above, and the percent change in viscosity and percent change in elasticity for the treated menses simulant as compared to the untreated menses simulant was determined. The percent change in viscosity was determined by subtracting the viscosity of the treated sample from the viscosity of the untreated sample and dividing the difference by the viscosity of the untreated sample. Percent change in elasticity was calculated in a similar manner. The percent change in fouling for the treated menses simulant samples was also determined as described above. The results are given in Table 3, with a negative (−) percentage indicating a decrease in viscosity, elasticity, or fouling, and a positive (+) percentage indicating an increase in fouling.

TABLE 3

| Treatment | Δ Viscosity | Δ Elasticity | Δ Fouling |
|---|---|---|---|
| 1 wt. % Sodium Citrate | −52% | −51% | +30% |
| 1 wt. % Dextran | −11% | −17% | −28% |
| 1 wt. % Cysteine | −51% | −63% | +36% |
| 1 wt. % PEG 600 lauryl ether | −47% | −57% | −58% |
| 1 wt. % PEG 600 monolaurate | −45% | −44% | −25% |
| 0.5 wt. % Sodium Citrate + 0.5 wt. % PEG 600 monolaurate | −65% | −67% | −55% |
| 1 wt. % Glucopon | −50% | −52% | −49% |

As can be seen from these results, all treatment agents reduced the viscosity and elasticity of menses simulant as compared to untreated controls, under the tested conditions. Five of the seven agents tested improved fouling, with the PEG 600 lauryl ether treated menses simulant having the greatest improvement in fouling. Two of the treatment agents, sodium citrate and cysteine, actually increased the fouling effect of the menses simulant, by 30% and 36%, respectively. Surprisingly, however, menses simulant treated with the combination of 0.5 wt. % sodium citrate and 0.5 wt. % PEG 600 monolaurate, showed an improvement in fouling, and the improvement was greater than when 1 wt. % PEG 600 monolaurate was added alone.

Example 4

Effect of PEG 600 Lauryl Ether and PEG 600 Monolaurate on Intake Times

In this example, the effect on intake time of polyethylene glycol 600 lauryl ether and polyethylene glycol 600 monolaurate added directly to a menses simulant was tested.

Treated menses simulant samples were prepared by adding 19.8 grams of menses simulant (prepared as described above) into a 30 mL beaker. 0.2 grams of liquid surfactant (either polyethylene glycol 600 lauryl ether or polyethylene glycol 600 monolaurate) was added dropwise to the menses simulant to yield a 1 wt % surfactant solution in simulant. The simulant/surfactant admixture was mixed for 20 minutes as described above.

Intake time was measured as the time required for treated or untreated menses simulant to penetrate into a standard absorbent composite. Absorbent composites were prepared that consisted of: 1) a bottom, airlaid absorbent layer (0.12 g/cm$^3$ density, 175 g/m$^2$ basis weight, 10% bico fiber, 90% pulp); and 2) a top layer of an aperatured spunbond cover (Coronop Ultra cover material, purchased from BBA Fiberweb, Surrey, England). The top and bottom layers of the composite were cut to 4"×4".

The intake time for treated and untreated menses simulant into absorbent composites was performed as follows:

An intake rate test block (as described above) was fitted with a small funnel and placed in the center of the absorbent composite sample on top of the cover material. The absorbent composite sample was insulted ("Gush 1") with 2 mL of treated or untreated menses simulant (prepared as described above), by injecting the simulant into the rate block funnel using a 5 mL pipette. The intake time for absorption (in seconds) was measured with a stopwatch and documented. A second insult ("Gush 2") was performed after 9 minutes and the second intake time was documented. This procedure was performed using three different absorbent composites for each treatment group. The results were averaged, and the percent change in intake time for the treated simulant samples as compared to the untreated control sample was determined. The percent change in intake time was determined by subtracting the intake time for the treated sample from the intake time for the untreated sample and dividing the difference by the intake time for the untreated sample. The results are set forth in Table 4 below.

TABLE 4

| | Gush 1 Intake Time (sec) | | | | | Gush 2 Intake Time (sec) | | | | |
|---|---|---|---|---|---|---|---|---|---|---|
| Sample | Rep1 | Rep2 | Rep3 | Ave | % Δ | Rep1 | Rep2 | Rep3 | Ave | % Δ |
| Control untreated simulant | 9.10 | 9.43 | 7.97 | 8.86 | — | 17.9 | 19.9 | 18.8 | 18.9 | — |
| Simulant + 1 wt % PEG 600 monolaurate | 6.31 | 6.25 | 6.12 | 6.28 | −29% | 14.2 | 12.8 | 12.6 | 13.2 | −30% |

TABLE 4-continued

| Sample | Gush 1 Intake Time (sec) | | | | | Gush 2 Intake Time (sec) | | | | |
|---|---|---|---|---|---|---|---|---|---|---|
| | Rep1 | Rep2 | Rep3 | Ave | % Δ | Rep1 | Rep2 | Rep3 | Ave | % Δ |
| Control untreated simulant | 10.7 | 9.60 | 8.60 | 9.64 | | 20.8 | 23.9 | 21.3 | 22.0 | |
| Simulant + 1 wt % PEG lauryl ether | 5.52 | 5.43 | 4.96 | 5.30 | −45% | 14.8 | 12.8 | 11.5 | 13.0 | −41% |

As can be seen from these results, menses simulant treated with 1 wt. % PEG 600 lauryl ether or 1 wt. % PEG 600 monolaurate had significantly lower (improved) intake times as compared with untreated menses simulant.

Example 5

Effect of PEG 600 Lauryl Ether Treatment of an Absorbent Composite on Intake Times In this example, the effect on intake time of PEG 600 lauryl ether, applied to the cover material and intake layer of an absorbent composite, was tested.

Intake time was measured as the time required for an untreated menses simulant to penetrate into a standard absorbent composite that was either untreated or treated with PEG 600 lauryl ether as described below.

Absorbent composites were prepared that consisted of: 1) a bottom, airlaid absorbent layer, available from Concert Fabrication (Thurso QC, Canada) (0.12 g/cm$^3$ density, 225 g/m$^2$ basis weight, 15% SAP (Degussa FAVOR SXM-9394); 10% bico fiber (Fiber Visions, ESC806); 75% Koch Golden Isles 4881 pulp; SAP distributed through the forming heads at 3:9:3; pulp and bico distributed evenly between the forming heads); 2) a middle intake layer of low density airlaid surge (150 g/m$^2$ basis weight, 0.94 mm thickness, 0.16 g/cm$^3$ density, 10% bico fiber (Fiber Visions, ESC806), 75% Koch Golden Isles 4881 pulp, 15% SAP (Degussa FAVOR SXM-9394); and 3) a top layer of an aperatured spunbond cover (Coronop Ultra cover material, purchased from BBA Fiberweb, Surrey, England). The top and bottom layers of the composite were cut to 4"×4" and the middle layer was 2.3"× 4".

Treated absorbent composites were prepared by applying PEG 600 lauryl ether to the intake and cover layers. The PEG 600 lauryl ether was applied to the intake layer by spraying undiluted surfactant (heated to about 50° C.) onto the intake layer using an atomizer. To determine the amount of surfactant applied to the intake layer, square pieces of the airlaid intake material were cut (approximately 20 cm×20 cm) and weighed. A small amount of surfactant was sprayed uniformly onto the fabric, and the treated material (airlaid plus surfactant) was weighed again. This process was repeated until the intake layer comprised an add-on amount of surfactant of 3% (by weight of the treated intake layer).

The PEG 600 lauryl ether was applied to the spunbound cover material via a "dip and nip" process. A pre-weighed, 20 cm×20 cm piece of the spunbond cover was dipped into a solution of PEG 600 lauryl ether in water. The wet spunbond was passed through a pair of calendar rolls (the "nip") to squeeze out most of the liquid, and the damp spunbond was immediately reweighed, before any significant evaporation occurred, to determine the amount of wet add-on for the spunbond material and calendar rolls being used. This wet add-on level, together with the concentration of the surfactant in the surfactant bath, determined the final level of surfactant add-on. The concentration of the surfactant bath was then adjusted so that the dry add-on amount of surfactant was 10% (by weight of the treated cover).

The intake time for treated and untreated absorbent composites was determined as described in Example 4, except using untreated menses simulant for the insults. This procedure was performed using five different absorbent composites for each treatment group. The results were averaged, and the percent change in intake time for the treated composites as compared to the untreated control was determined. The percent change in intake time was determined by subtracting the intake time for the treated sample from the intake time for the untreated sample and dividing the difference by the intake time for the untreated sample. The results are set forth in Table 5 below.

TABLE 5

| Treatment | Rep1 | Rep2 | Rep3 | Rep4 | Rep5 | Ave. | % Δ |
|---|---|---|---|---|---|---|---|
| | Gush 1 Intake Time (sec) | | | | | | |
| Untreated control | 31 | 38 | 32 | 19 | 30 | 30 | — |
| Treated with PEG 600 lauryl ether | 20 | 16 | 22 | 14 | 13 | 17 | −43% |
| | Gush 2 Intake Time (sec) | | | | | | |
| Untreated control | 140 | 163 | 146 | 196 | 167 | 162 | — |
| Treated with PEG 600 lauryl ether | 69 | 74 | 72 | 84 | 76 | 75 | −54% |

As can be seen from these results, the composite samples that were treated with PEG 600 lauryl ether improved intake time for both the first and second insults as compared to the untreated composites.

Example 6

Effect of Various Surfactants on Intake Times

In this example, the effect on intake time of PEG 200 monolaurate, PEG 400 monolaurate, PEG 600 monolaurate, PEG 1000 monolaurate, PEG 4000 monolaurate, PEG 600 dilaurate, PEG 600 distearate, PEG 200 monoisostearate, PEG 600 monoisostearate, PEG 4000 monostearate, PEG 200 monooleate, PEG 600 monooleate, PEG 1540 monooleate, PEG 600 dioleate, PEG 1540 dioleate, glycerol monostearate, sorbitan monolaurate, polyoxyethylene (POE) sorbitol oleate laurate, sucrose dioleate, stearyl alcohol, ammonium laurate, ammonium oleate, sodium citrate plus PEG 600 monolaurate, iconol 24-12 (i.e., PEG 600 lauryl ether), iconol 24-9 (i.e., PEG 600 lauryl ether), Triton X100, and calcium chloride added directly to a menses simulant was tested.

To prepare the treated menses simulant, 24.5 milliliters (mL) of menses simulant (prepared as described above) was weighed into a 30-mL beaker. For 27 of the 36 treated samples, 0.5 mL of liquid surfactant or 0.5 g of solid surfactant (one of PEG 200 monolaurate, PEG 400 monolaurate, PEG 600 monolaurate, PEG 1000 monolaurate, PEG 4000 monolaurate, PEG 600 dilaurate, PEG 600 distearate, PEG 200 monoisostearate, PEG 600 monoisostearate, PEG 4000 monoisostearate, PEG 200 monooleate, PEG 600 monooleate, PEG 1540 monooleate, PEG 600 dioleate, PEG 1540 dioleate, glycerol monostearate, sorbitan monolaurate, POE sorbitol oleate laurate, sucrose dioleate, stearyl alcohol, ammonium laurate, ammonium oleate, iconol 24-12, iconol 24-9, Triton X100, or calcium chloride) was added to the menses to yield a 2 wt % surfactant solution in simulant. One additional sample was made using a combination of PEG 600 monolaurate and sodium citrate. Specifically, the sample added equivalent amounts of sodium citrate and PEG 600 monolaurate (i.e., 0.25 mL PEG 600 monolaurate and 0.25 mL sodium citrate) to the menses simulant to yield a 2 wt % surfactant solution in simulant.

For the remaining 9 samples, less surfactant was used. Specifically, 2 samples contained 1 wt % surfactant (by adding 0.25 mL or 0.25 g of either PEG 600 monolaurate or calcium chloride); 2 samples contained 0.5 wt % surfactant (by adding 0.12 mL or 0.12 g of either PEG 600 monolaurate or calcium chloride); and one sample contained 0.25 wt % surfactant (by adding 0.06 mL PEG 600 monolaurate). Additionally, 4 samples used a combination of PEG 600 monolaurate and sodium citrate to treat the menses simulant. Specifically, in one sample, equivalent amounts of sodium citrate and PEG 600 monolaurate (i.e., 0.12 mL PEG 600 monolaurate and 0.12 g sodium citrate) were added to the menses simulant to yield a 1 wt % surfactant solution in simulant; one sample combined 0.25 g sodium citrate and 0.12 mL PEG 600 monolaurate and added the combination to the menses simulant to yield 1.5 wt % surfactant solution in simulant; and one sample combined 0.25 mL PEG 600 monolaurate and 0.12 g sodium citrate and added the combination to the menses simulant to yield 1.5 wt % surfactant solution in simulant. A small magnetic stir bar (approximately 0.5 inches long) was placed in the solution and the solution was stirred at about 4 rpm for 30 minutes to thoroughly mix. During mixing, a piece of polyethylene film (1/16 inch thick by 1 1/8 inch diameter-the approximate inner diameter of the 30-mL beaker) was floated on top of the treated menses solution to protect the simulant from denaturation. After sufficient mixing, the treated menses solution was poured through a filter to remove clumps of surfactant particles.

Intake time was measured as the time required for an untreated or treated menses simulant to penetrate into a standard absorbent composite.

Absorbent composites were prepared that consisted of: 1) a bottom, airlaid absorbent layer (0.12 g/cm$^3$ density, 175 g/m$^2$ basis weight, 10% bico fiber, 90% pulp); and 2) a top layer of an aperatured spunbond cover (Coronop Ultra cover material, purchased from BBA Fiberweb, Surrey, England). The top and bottom layers of the composite were cut to 4"×4".

Fourteen control samples comprising untreated menses simulant were prepared as described above. Each control sample was prepared from the same simulant batch as was used to prepare the treated menses simulant to which it is compared. (As will be seen more clearly below, the surfactant treated simulants will be grouped in the tables under their respective control sample.) Each batch of simulant was prepared on a different day.

The intake time for treated and untreated menses simulants into the absorbent composites was performed as described in Example 4.

This procedure was performed using three different absorbent composites for each treatment group. The results were averaged, and the percent change in intake time for the treated simulant samples as compared to the untreated control samples was determined. The percent change in intake time was determined by subtracting the intake time from the treated sample from the intake time for the untreated sample and dividing the difference by the intake time for the untreated sample. The results are set forth in Table 6 below.

TABLE 6

| Sample | Gush 1 Intake Time (sec) | | | | | Gush 2 Intake Time (sec) | | | | |
|---|---|---|---|---|---|---|---|---|---|---|
| | Rep1 | Rep2 | Rep3 | Ave | % Δ | Rep1 | Rep2 | Rep3 | Ave | % Δ |
| Control untreated simulant A | 10.54 | 12.01 | 11.05 | 11.20 | — | 22.99 | 26.52 | 16.65 | 22.05 | — |
| 2 wt. % PEG 200 Monolaurate | 7.02 | 10.29 | 7.33 | 8.21 | −27% | 12.45 | 16.16 | 14.08 | 14.23 | −35% |
| 2 wt. % PEG 600 Monolaurate | 4.38 | 4.77 | — | 4.58 | −59% | 7.08 | 7.71 | — | 7.40 | −66% |
| Control untreated simulant B | 6.63 | 6.61 | 6.65 | 6.63 | — | 11.19 | 11.94 | 13.44 | 12.19 | — |
| 2 wt. % PEG 4000 Monolaurate | 5.75 | 5.82 | 5.66 | 5.74 | −13% | 8.43 | 8.02 | 9.75 | 8.73 | −28% |
| Control untreated simulant C | 7.87 | 7.38 | 6.40 | 7.22 | — | 11.22 | 12.66 | 13.44 | 12.44 | — |
| 2 wt. % PEG 4000 monostearate | 7.91 | 7.74 | 8.34 | 8.00 | 11% | 17.25 | 16.95 | 45.02 | 26.41 | +112% |
| Control untreated simulant D | 8.37 | 8.46 | 7.49 | 8.11 | — | 12.18 | 15.87 | 14.13 | 14.06 | — |
| 2 wt. % PEG 600 distearate | 5.62 | 6.06 | 6.25 | 5.98 | −26% | 10.38 | 9.00 | 8.13 | 9.17 | −35% |
| Control untreated simulant E | 5.84 | 6.36 | 6.63 | 6.28 | — | 8.63 | 10.06 | 10.12 | 9.60 | — |

TABLE 6-continued

| | Gush 1 Intake Time (sec) | | | | | Gush 2 Intake Time (sec) | | | | |
|---|---|---|---|---|---|---|---|---|---|---|
| Sample | Rep1 | Rep2 | Rep3 | Ave | % Δ | Rep1 | Rep2 | Rep3 | Ave | % Δ |
| 2 wt. % PEG 600 dilaurate | 4.29 | 3.79 | 3.66 | 3.91 | −38% | 15.19 | 14.60 | 13.13 | 14.31 | +49% |
| Control untreated simulant F | 6.95 | 5.99 | 5.69 | 6.21 | — | 10.84 | 9.84 | 9.31 | 10.00 | — |
| 2 wt. % PEG 600 monoisostearate | 4.71 | 6.51 | 5.42 | 5.55 | −11% | 7.39 | 6.06 | 5.98 | 6.48 | −35% |
| Control untreated simulant G | 10.2 | 11.1 | 9.9 | 10.4 | — | 26.4 | 24.2 | 25.1 | 23.2 | — |
| 2 wt. % PEG 600 monooleate | 5.8 | 6.4 | 6.7 | 6.3 | −39% | 8.9 | 9.2 | 9.7 | 9.3 | −63% |
| Control untreated simulant H | 10.54 | 7.69 | 0.00 | 6.08 | — | 16.63 | 14.86 | 0.00 | 10.50 | — |
| 2 wt. % PEG 400 monolaurate | 4.54 | 4.88 | 4.47 | 4.63 | −24% | 7.63 | 8.56 | 8.25 | 8.15 | −22% |
| Control untreated simulant I | 10.00 | 7.91 | 8.53 | 8.81 | — | 23.41 | 20.63 | 22.56 | 22.20 | — |
| 2 wt. % Glycerol Monostearate | 6.53 | 4.97 | 6.87 | 6.12 | −31% | 15.12 | 12.94 | 9.40 | 12.49 | +29% |
| 2 wt. % PEG 600 dioleate | 8.07 | 8.37 | 7.47 | 7.97 | −10% | 24.38 | 24.50 | 18.30 | 22.39 | +1% |
| 2 wt. % Sorbitan monolaurate | 6.81 | 7.81 | 6.93 | 7.18 | −18% | 27.28 | 25.59 | 29.78 | 27.55 | +24% |
| Control untreated simulant J | 9.19 | 9.43 | 7.97 | 8.86 | — | 17.91 | 19.94 | 18.78 | 18.88 | — |
| 2 wt. % PEG 1540 dioleate | 6.63 | 5.37 | 6.31 | 6.10 | −31% | 17.72 | 15.87 | 19.37 | 17.65 | −6% |
| 1 wt % PEG 600 monolaurate | 6.25 | 6.12 | 6.31 | 6.23 | −30% | 14.22 | 12.82 | 12.60 | 13.21 | −30% |
| 0.5 wt % PEG 600 monolaurate | 5.00 | 5.28 | 4.91 | 5.06 | −43% | 10.94 | 10.97 | 11.75 | 11.22 | −41% |
| 0.25 wt % PEG 600 monolaurate | 8.16 | 7.22 | 7.40 | 7.59 | −14% | 15.84 | 16.19 | 17.09 | 16.37 | −13% |
| 2 wt. % PEG 200 monooleate | 7.00 | 6.19 | 8.68 | 7.29 | −18% | 31.25 | 36.35 | 35.47 | 34.36 | +82% |
| 2 wt. % PEG 1540 monooleate | 5.41 | 7.00 | 6.69 | 6.37 | −28% | 14.44 | 16.47 | 17.91 | 16.27 | −14% |
| 2 wt. % PEG 200 monoisostearate | 8.81 | 8.25 | 8.07 | 8.38 | −5% | 24.50 | 24.07 | 27.03 | 25.20 | +33% |
| 0.5 wt % PEG 600 monolaurate + 0.5 wt % sodium citrate | 4.16 | 3.37 | 3.82 | 3.78 | −57% | 7.41 | 6.88 | 7.59 | 7.29 | −61% |
| 1 wt % PEG 600 monolaurate + 0.5 wt % sodium citrate | 3.43 | 3.84 | 3.97 | 3.75 | −58% | 8.13 | 7.66 | 9.10 | 8.30 | −56% |
| 0.5 wt % PEG 600 monolaurate + 1 wt % sodium citrate | 4.22 | 4.57 | 4.63 | 4.47 | −50% | 11.09 | 10.78 | 11.50 | 11.12 | −41% |
| 1 wt % PEG 600 monolaurate + 1 wt % sodium citrate | 5.43 | 5.30 | 5.27 | 5.33 | −46% | 12.47 | 12.94 | 13.20 | 12.87 | −17% |
| Control untreated simulate K | 10.70 | 9.60 | 8.60 | 9.63 | — | 20.75 | 23.88 | 21.34 | 21.99 | — |
| 2 wt. % POE sorbitol oleate laurate | 6.98 | 7.77 | 7.74 | 7.50 | −22% | 18.60 | 20.13 | 20.04 | 19.59 | −11% |
| 2 wt. % Sucrose dioleate | 9.99 | 10.49 | 9.76 | 10.08 | +5% | 310.0 | 306.0 | 312.0 | 309.3 | +1307% |
| 2 wt. % Stearyl alcohol | 6.30 | 6.34 | 7.68 | 6.77 | −30% | 17.55 | 15.06 | 16.34 | 16.32 | −26% |
| 2 wt. % Iconol 24-12 | 6.56 | 6.70 | 6.61 | 6.62 | −31% | 16.14 | 16.91 | 17.70 | 16.92 | −23% |
| 2 wt. % Iconol 24-9 | 5.52 | 5.43 | 4.96 | 5.30 | −45% | 14.86 | 12.77 | 11.50 | 13.04 | −41% |
| Control untreated simulant L | 8.90 | 8.02 | 8.49 | 8.47 | — | 22.63 | 20.43 | 23.05 | 22.04 | — |

TABLE 6-continued

| Sample | Gush 1 Intake Time (sec) | | | | | Gush 2 Intake Time (sec) | | | | |
|---|---|---|---|---|---|---|---|---|---|---|
| | Rep1 | Rep2 | Rep3 | Ave | % Δ | Rep1 | Rep2 | Rep3 | Ave | % Δ |
| 2 wt. % Ammonium laurate | 10.40 | 9.77 | 9.91 | 10.03 | 18% | — | — | — | — | — |
| 2 wt. % Ammonium oleate | 8.02 | 7.55 | 8.48 | 8.02 | −5% | 20.05 | 20.10 | 24.52 | 21.56 | −2% |
| Control untreated simulate M | 9.73 | 9.54 | 8.71 | 9.33 | — | 17.13 | 18.36 | 19.67 | 18.39 | — |
| 2 wt. % Triton X100 | 7.36 | 7.17 | 7.63 | 7.39 | −21% | 20.41 | 21.24 | 19.84 | 20.54 | 11% |
| 0.5 wt % calcium chloride | 10.95 | 9.40 | 9.00 | 9.78 | 5% | 120.0 | 124.0 | 90.00 | 111.3 | +506% |
| 1 wt % calcium chloride | 10.40 | 13.40 | 12.41 | 12.07 | 29% | 35.22 | 63.55 | 41.97 | 46.91 | 155% |
| 2 wt % calcium chloride | 17.35 | 15.95 | 16.45 | 16.58 | 78% | — | — | — | — | — |
| Control untreated simulant N | 10.46 | 11.45 | 11.88 | 11.26 | — | 21.84 | 18.74 | 19.82 | 20.13 | — |
| 2 wt. % PEG 1000 monolaurate | 7.67 | 8.09 | 7.57 | 7.78 | −31% | 17.30 | 20.33 | 19.07 | 18.90 | −6% |
| 2 wt. % PEG 600 dioleate | 8.23 | 9.31 | 8.61 | 8.72 | −23% | 30.65 | 33.03 | 29.82 | 31.17 | 55% |

As can be seen from these results, the menses simulant samples that were treated with 2 wt. % PEG 200 monolaurate, 2 wt. % PEG 600 monolaurate, 2 wt. % PEG 4000 monolaurate, 2 wt. % PEG 600 distearate, 2 wt. % PEG 600 monoisostearate, 2 wt. % PEG 400 monolaurate, 2 wt. % PEG 1540 dioleate, 1 wt % PEG 600 monolaurate, 0.5 wt % PEG 600 monolaurate, 0.25 wt % PEG 600 monolaurate, 2 wt. % PEG 600 monooleate, 2 wt. % PEG 1540 monooleate, 2 wt. % POE Sorbitol oleate laurate, 2 wt. % stearyl alcohol, 2 wt. % ammonium oleate, 2 wt. % PEG 1000 monolaurate, 2 wt. % Iconol 24-12, 2 wt. % Iconol 24-9, and all combinations of PEG 600 monolaurate and sodium citrate improved intake time for both the first and second insults as compared to the untreated controls. The simulant samples that were treated with 2 wt. % PEG 600 dilaurate, 2 wt. % glycerol monostearate, 2 wt. % PEG 600 dioleate, 2 wt. % sorbitan monolaurate, 2 wt. % PEG 200 monooleate, 2 wt. % PEG 200 monoisostearate, and 2 wt. % PEG 600 dioleate improved intake time for the first insult as compared to the untreated controls.

The viscosity and elasticity of untreated menses simulant and menses simulant treated with the various surfactants were tested using a Vilastic III Capillary Rheometer, under the conditions as described above, and the percent change in viscosity and percent change in elasticity for the treated menses simulant as compared to the untreated menses simulant was determined. The percent change in viscosity was determined by subtracting the viscosity of the treated sample from the viscosity of the untreated sample and dividing the difference by the viscosity of the untreated sample. Percent change in elasticity was calculated in a similar manner. The results are given in Table 7.

TABLE 7

| Sample | Viscosity (cPs) | % Δ Viscosity | Elasticity (cPs) | % Δ Elasticity |
|---|---|---|---|---|
| Control untreated simulant A | 22.97 | — | 4.44 | — |
| 2 wt. % PEG 200 Monolaurate | 53.59 | +133% | 20.42 | +360% |
| 2 wt. % PEG 600 Monolaurate | 9.80 | −57% | 0.56 | −87% |
| Control untreated simulant B | 25.11 | — | 5.35 | — |
| 2 wt. % PEG 4000 Monolaurate | 18.70 | −26% | 2.65 | −50% |
| Control untreated simulant C | 26.32 | — | 6.75 | — |
| 2 wt. % PEG 4000 monostearate | 20.47 | −22% | 2.40 | −64% |
| Control untreated simulant D | 23.38 | — | 4.58 | — |
| 2 wt. % PEG 600 distearate | 24.99 | +7% | 3.65 | −20% |
| Control untreated simulant E | 23.38 | — | 4.58 | — |
| 2 wt. % PEG 600 dilaurate | 9.10 | −61% | 1.47 | −68% |
| Control untreated simulant F | 23.00 | — | 4.73 | — |
| 2 wt. % PEG 600 monoisostearate | 24.67 | +7% | 4.56 | −4% |
| Control untreated simulant G | 23.66 | — | 3.98 | — |
| 2 wt. % PEG 600 monooleate | 13.44 | −43% | 1.66 | −58% |

TABLE 7-continued

| Sample | Viscosity (cPs) | % Δ Viscosity | Elasticity (cPs) | % Δ Elasticity |
|---|---|---|---|---|
| Control untreated simulant H | 21.79 | — | 4.09 | — |
| 2 wt. % PEG 400 monolaurate | 7.11 | −67% | 1.68 | −59% |
| Control untreated simulant I | 23.14 | — | 4.22 | — |
| 2 wt. % Glycerol Monostearate | 22.10 | −4% | 4.58 | +9% |
| 2 wt. % PEG 600 dioleate | 17.43 | −25% | 3.48 | −18% |
| 2 wt. % Sorbitan monolaurate | 44.31 | +91% | 10.06 | 138% |
| Control untreated simulant J | 23.95 | — | 5.60 | — |
| 2 wt. % PEG 1540 dioleate | 13.40 | −44% | 1.82 | −68% |
| 1 wt % PEG 600 monolaurate | 10.58 | −56% | 1.31 | −77% |
| 0.5 wt % PEG 600 monolaurate | 10.66 | −55% | 2.32 | −59% |
| 0.25 wt % PEG 600 monolaurate | 21.62 | −10% | 4.76 | −15% |
| 2 wt. % PEG 200 monooleate | 62.49 | +161% | 12.24 | +119% |
| 2 wt. % PEG 1540 monooleate | 17.99 | −25% | 2.85 | −49% |
| 2 wt. % PEG 200 monoisostearate | 18.96 | −21% | 4.10 | −27% |
| 0.5 wt % PEG 600 monolaurate + 0.5 wt % sodium citrate | 6.40 | −73% | 2.12 | −62% |
| 1 wt % PEG 600 monolaurate + 0.5 wt % sodium citrate | 8.15 | −66% | 1.03 | −82% |
| 0.5 wt % PEG 600 monolaurate + 1 wt % sodium citrate | 7.87 | −67% | 0.57 | −90% |
| 1 wt % PEG 600 monolaurate + 1 wt % sodium citrate | 9.50 | −60% | 98.25 | +1654% |
| Control untreated simulate K | 47.40 | — | 10.82 | — |
| 2 wt. % POE sorbitol oleate laurate | 17.72 | −63% | 2.11 | −80% |
| 2 wt. % Sucrose dioleate | 40.91 | −14% | 9.93 | −8% |
| 2 wt. % Stearyl alcohol | 19.72 | −58% | 3.52 | −67% |
| 2 wt. % Iconol 24-12 | 15.08 | −68% | 2.56 | −76% |
| 2 wt. % Iconol 24-9 | 5.13 | −89% | 1.84 | −83% |
| Control untreated simulant L | 17.39 | — | 3.26 | — |
| 2 wt. % Ammonium laurate | 22.03 | +27% | 2.91 | −11% |
| 2 wt. % Ammonium oleate | 18.00 | +4% | 3.66 | +12% |
| Control untreated simulate M | 29.67 | — | 7.35 | — |
| 2 wt. % Triton X100 | 1.06 | −96% | 0.72 | −90% |
| 0.5 wt % calcium chloride | 9.66 | −67% | 1.74 | −76% |
| 1 wt % calcium chloride | 15.86 | −47% | 2.77 | −62% |
| 2 wt % calcium chloride | 10.21 | −66% | 2.20 | −70% |
| Control untreated simulant N | 47.96 | — | 12.66 | — |
| 2 wt. % PEG 1000 monolaurate | 27.47 | −43% | 4.19 | −67% |
| 2 wt. % PEG 600 dioleate | 24.12 | −50% | 3.79 | −70% |

As can be seen from these results, simulants treated with 2 wt. % PEG 600 monolaurate, 2 wt. % PEG 4000 monolaurate, 2 wt. % PEG 4000 monostearate, 2 wt. % PEG 600 dilaurate, 2 wt. % PEG 600 monooleate, 2 wt. % PEG 400 monolaurate, 2 wt. % PEG 600 dioleate, 2 wt. % PEG 1540 dioleate, 1 wt % PEG 600 monolaurate, 0.5 wt % PEG 600 monolaurate, 0.25 wt % PEG 600 monolaurate, 2 wt. % PEG 1540 monooleate, 2 wt. % PEG 200 monoisostearate, the combination of 0.5 wt % PEG 600 monolaurate+0.5 wt % sodium citrate, the combination of 1 wt % PEG 600 monolaurate+0.5 wt % sodium citrate, the combination of 0.5 wt % PEG 600 monolaurate+1 wt % sodium citrate, 2 wt. % POE sorbitol oleate laurate, 2 wt. % sucrose dioleate, 2 wt. % stearyl alcohol, 2 wt. % Iconol 24-12, 2 wt. % Iconol 24-9, all concentrations of calcium chloride, 2 wt. % PEG 1000 monolaurate, 2 wt. % PEG 600 dioleate, or 2 wt. % Triton X100 reduced both viscosity and elasticity of menses simulant as compared to untreated controls, under the tested conditions. Composites treated with 2 wt. % PEG 600 distearate, 2 wt. % PEG 600 monoisostearate, or 2 wt. % ammonium laurate reduced elasticity of menses simulant as compared to untreated controls. Additionally, composites treated with 2 wt. % glycerol monostearate or the combination of 1 wt % PEG 600 monolaurate and 1 wt % sodium citrate reduced viscosity of menses simulant as compared to untreated controls.

When introducing elements of the present disclosure or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description and shown in the accompanying drawings shall be interpreted as illustrative and not in a limiting sense.

What is claimed is:

1. A personal care product for receiving a fluid having viscoelastic properties, said personal care product comprising a backsheet, an absorbent core, an intact layer, a body contact layer, and a treatment agent, wherein the treatment agent is present on at least one of the intake layer and the absorbent core in an amount of from about 3% (by weight of the treated substrate) to about 12% (by weight of the treated substrate) and wherein the treatment agent is polyethylene glycol 600 monolaurate.

2. The personal care product of claim 1 further comprising a viscoelastant agent selected from the group consisting of sodium citrate, dextran, cysteine, alkyl polyglycoside and combinations thereof.

3. The personal care product of claim 1 wherein the treatment agent comprises polyethylene glycol 600 monolaurate and sodium citrate.

4. The personal care product of claim 1 wherein the personal care product is selected from the group consisting of sanitary napkins, panty liners, tampons, interlabial pads, diapers, training pants, adult incontinence garments, sanitary wipes, and wound dressings.

5. The personal care product of claim 1 wherein the treatment agent is present on the intake layer.

6. The personal care product of claim 1 wherein the treatment agent is present on the absorbent core.

7. A personal care product for receiving a fluid having viscoelastic properties, said personal care product comprising a backsheet, an absorbent core, an intake layer, a body contact layer, and a treatment agent selected from the group consisting of polyethylene glycol laurates, polyethylene glycol lauryl ethers, and combinations thereof, wherein said treatment agent is capable of reducing the viscosity and elasticity of the fluid and is present on at least one of the intake layer and the absorbent core in an amount of from about 3% (by weight of the treated substrate) to about 12% (by weight of the treated substrate).

8. The personal care product of claim 7 wherein the treatment agent is capable of reducing the fouling effects of the fluid.

9. A personal care product for receiving a fluid having viscoelastic properties, said personal care product comprising a backsheet, an absorbent core, an intake layer, a body contact layer, and a polyethylene glycol derivative selected from the group consisting of polyethylene glycol lauryl ethers, PEG monooleates, PEG dioleates and PEG 16 octyl phenyl, wherein said polyethylene glycol derivative is capable of reducing the fouling effects of the fluid and is present on at least one of the intake layer and the absorbent core in an amount of from about 3% (by weight of the treated substrate) to about 12% (by weight of the treated substrate).

10. The personal care product of claim 9 wherein the polyethylene glycol derivative is capable of reducing the viscosity and elasticity of the fluid.

* * * * *